United States Patent
Tsumura et al.

(10) Patent No.: US 10,597,621 B2
(45) Date of Patent: Mar. 24, 2020

(54) ROTATING CULTURE VESSEL AND AUTOMATIC CELL CULTURE APPARATUS USING SAME

(71) Applicant: JTEC CORPORATION, Kobe-shi, Hyogo (JP)

(72) Inventors: Takashi Tsumura, Hyogo (JP); Hiromi Okada, Hyogo (JP); Toshimasa Uemura, Ibaraki (JP); Yoshimi Oyabu, Ibaraki (JP)

(73) Assignee: JTEC CORPORATION, Kobe-shi (JP)

( * ) Notice: Subject to any disclaimer, the term of this patent is extended or adjusted under 35 U.S.C. 154(b) by 0 days.

(21) Appl. No.: 16/365,524

(22) Filed: Mar. 26, 2019

(65) Prior Publication Data

US 2019/0225924 A1    Jul. 25, 2019

Related U.S. Application Data

(62) Division of application No. 13/375,606, filed as application No. PCT/JP2010/059754 on Jun. 9, 2010, now Pat. No. 10,287,539.

(30) Foreign Application Priority Data

Jun. 9, 2009  (JP) ................. 2009-138475

(51) Int. Cl.
   C12M 3/04        (2006.01)
   C12M 3/00        (2006.01)
(52) U.S. Cl.
   CPC ............ C12M 21/08 (2013.01); C12M 27/10 (2013.01); C12M 27/12 (2013.01)
(58) Field of Classification Search
   CPC ............................. C12M 27/12; C12M 27/10
   See application file for complete search history.

(56) References Cited

U.S. PATENT DOCUMENTS

| 4,988,623 A | 1/1991 | Schwarz |
|---|---|---|
| 5,262,055 A | 11/1993 | Bae |

(Continued)

FOREIGN PATENT DOCUMENTS

| JP | 2006-14675 A1 | 1/2006 |
|---|---|---|
| JP | 2006-115798 A1 | 5/2006 |

(Continued)

OTHER PUBLICATIONS

International Search Report for International Application No. PCT/JP2010/059754 dated Aug. 3, 2010.

*Primary Examiner* — Jonathan M Hurst
(74) *Attorney, Agent, or Firm* — Kratz, Quintos & Hanson, LLP

(57) ABSTRACT

Disclosed is a rotating culture vessel based on a rotating culture technology using an RWV, by which cell seeding, liquid medium exchange, quality control and so on can be automated and degassing can be conducted simultaneously with liquid medium exchange without disturbing the cells under culture. Also disclosed is an automatic cell culture apparatus using the same. A rotating culture vessel, which contains cells and a liquid culture medium, to be attached to a horizontal rotating shaft of a rotating culture device to three-dimensionally culture the cells, wherein one or more inlets/outlets for supplying cells and a liquid culture medium at the early stage and then taking out the cultured cells, are formed at appropriate position of a flat cylindrical culture container; at least one pair of a supply port and a discharge port for liquid medium exchange is provided on the outer circumferential cylindrical face of the culture container.

2 Claims, 20 Drawing Sheets

(56) References Cited

U.S. PATENT DOCUMENTS

| | | |
|---|---|---|
| 5,437,998 A | 8/1995 | Schwarz |
| 6,022,733 A | 2/2000 | Tam |
| 6,080,581 A | 6/2000 | Anderson |
| 2004/0110273 A1 | 6/2004 | Akers |
| 2007/0254356 A1 | 11/2007 | Wilson |
| 2009/0148941 A1 | 6/2009 | Florez |

FOREIGN PATENT DOCUMENTS

| | | |
|---|---|---|
| JP | 2006-149268 A1 | 6/2006 |
| JP | 2008-237203 A1 | 10/2008 |

[Fig. 1]
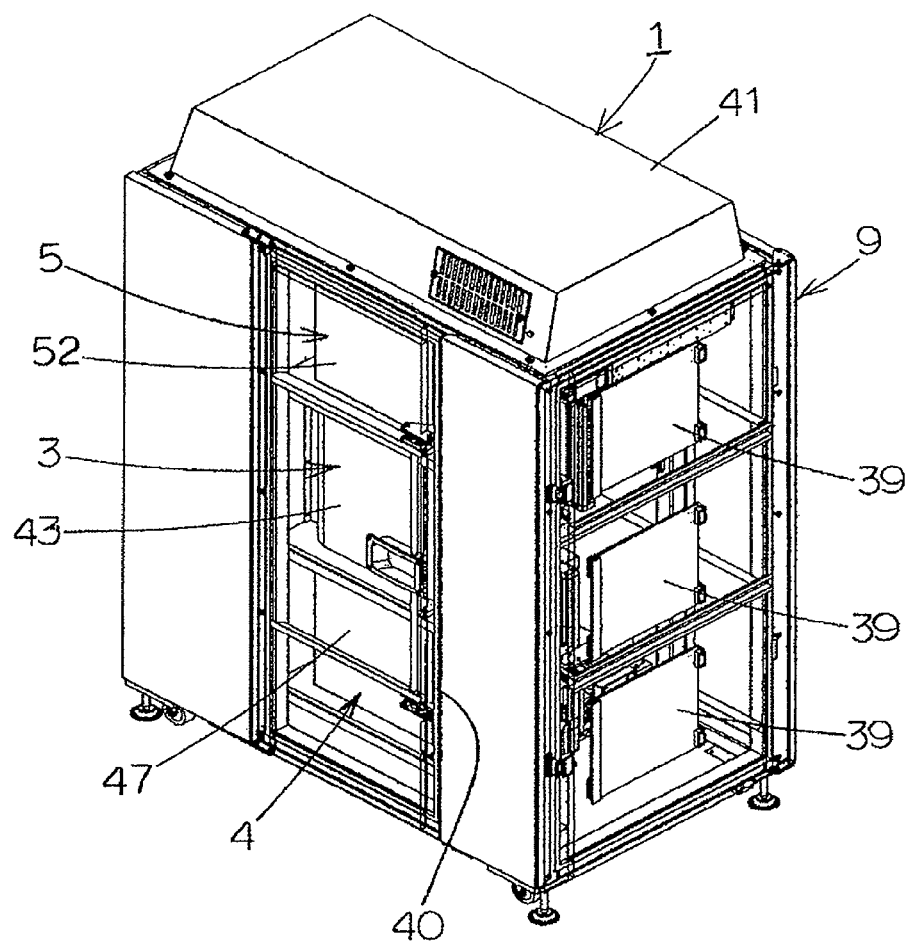

[Fig. 2]
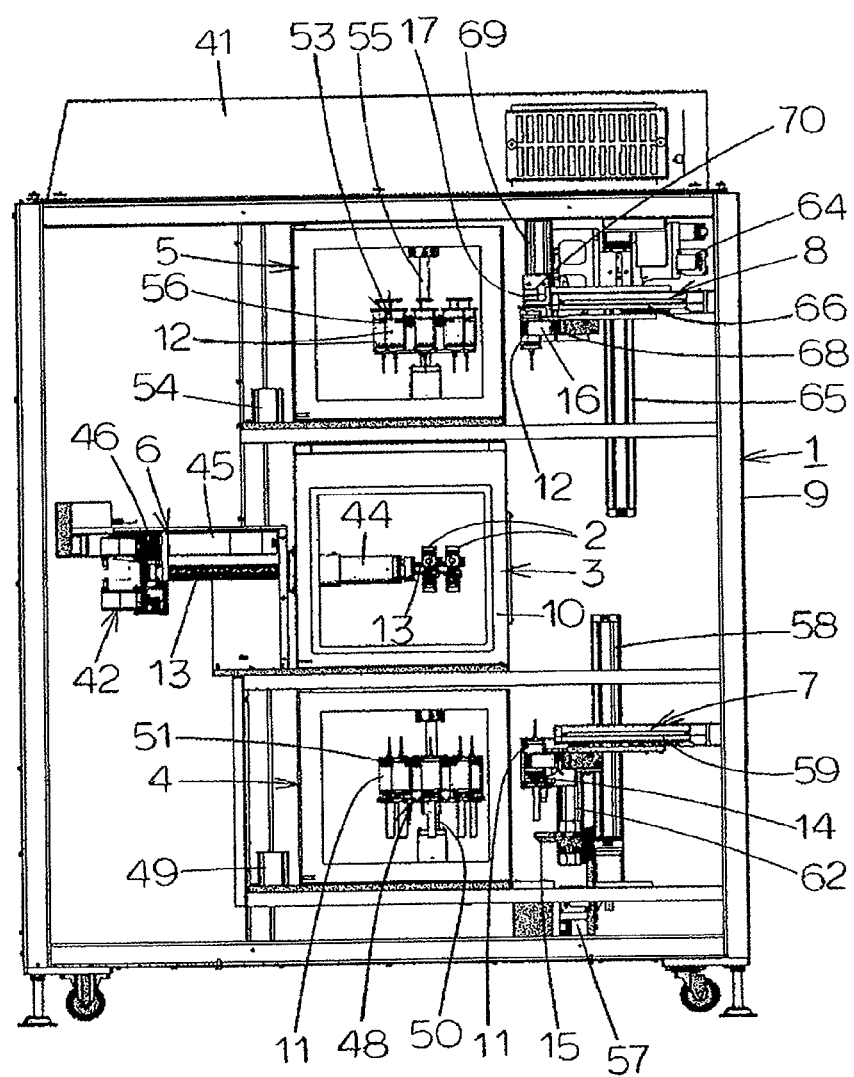

[Fig. 3]
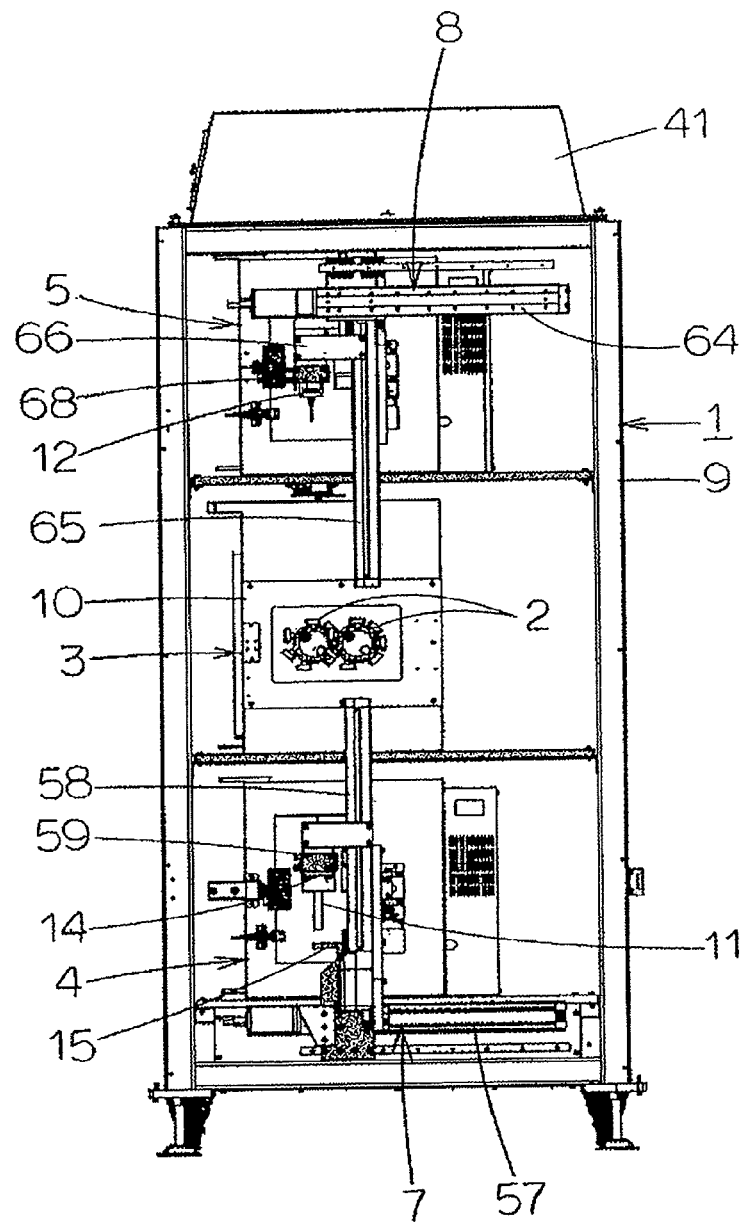

[Fig. 4]
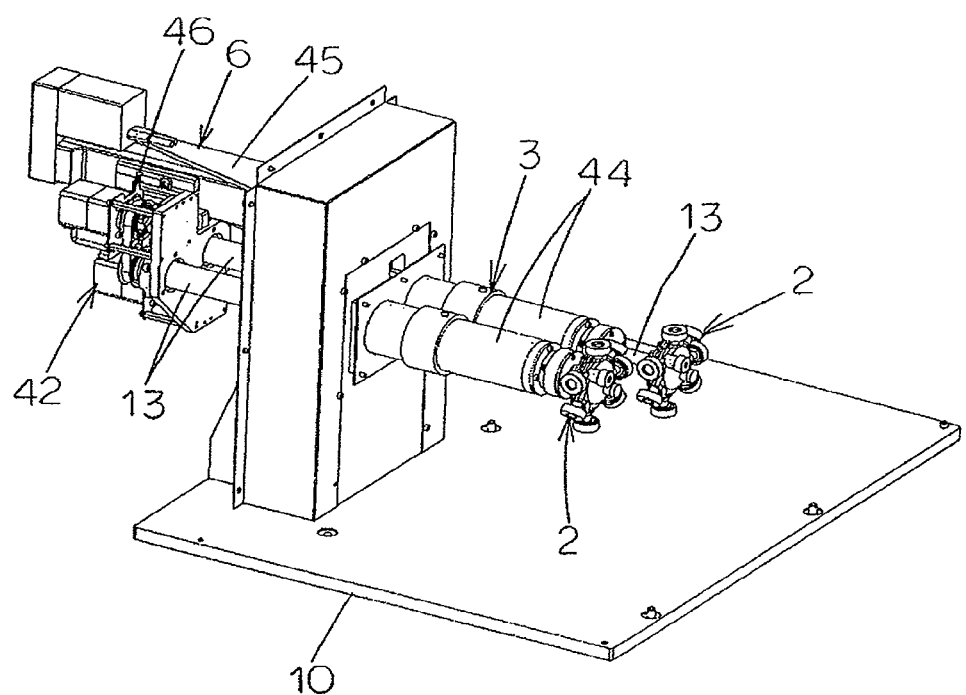

[Fig. 5]
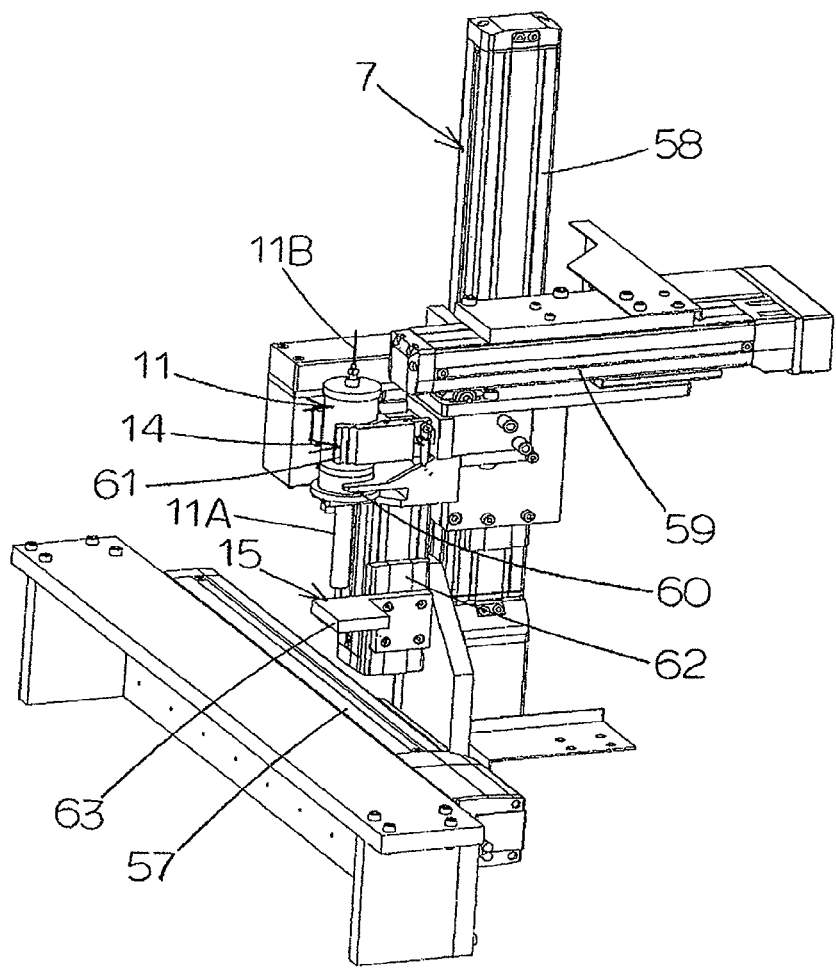

[Fig. 6]
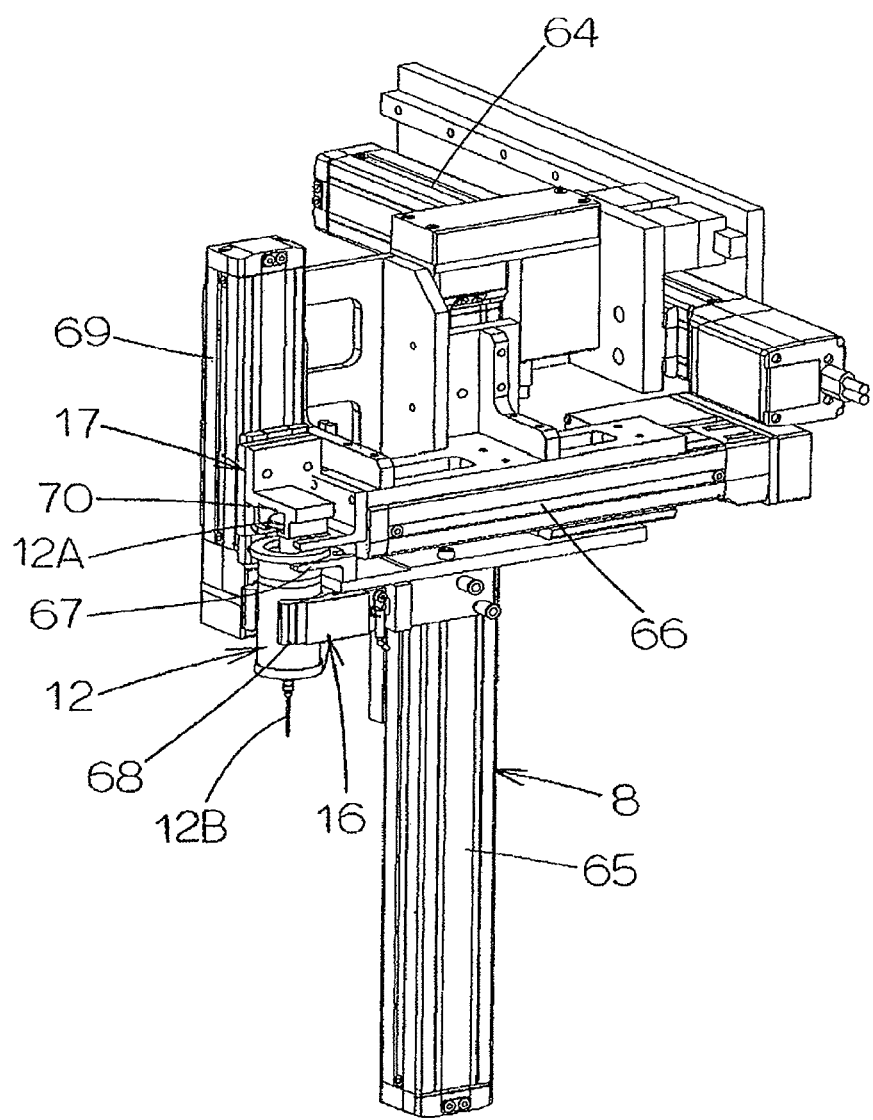

[Fig. 7]
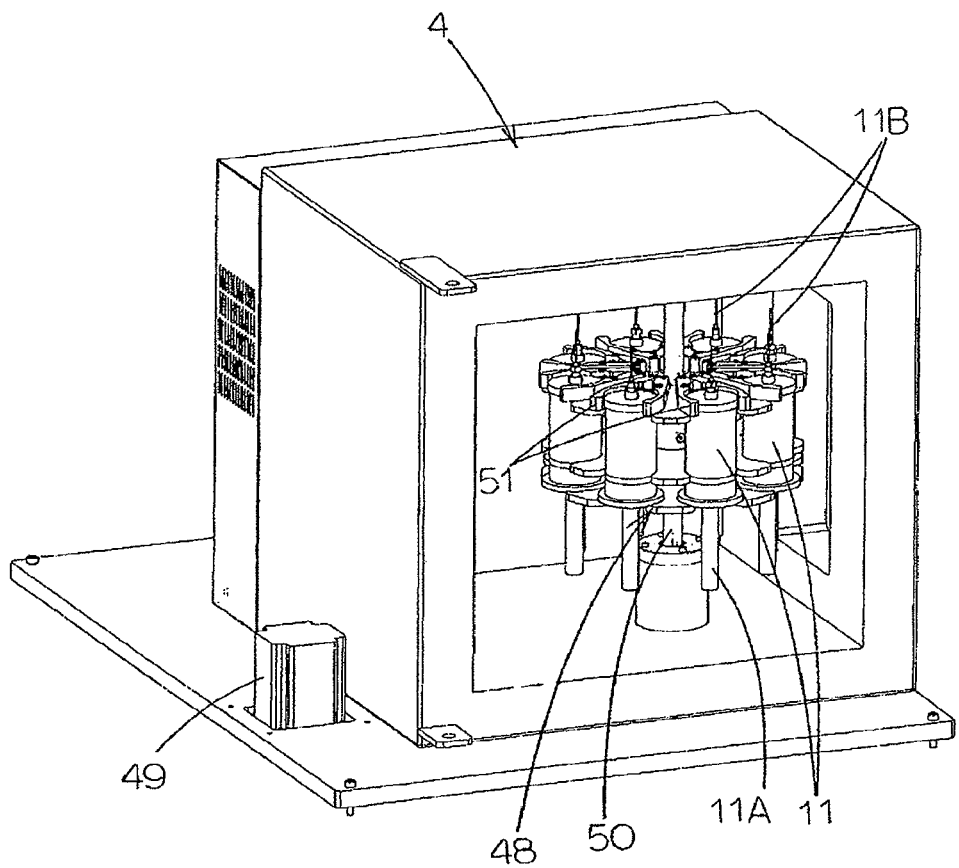

[Fig. 8]
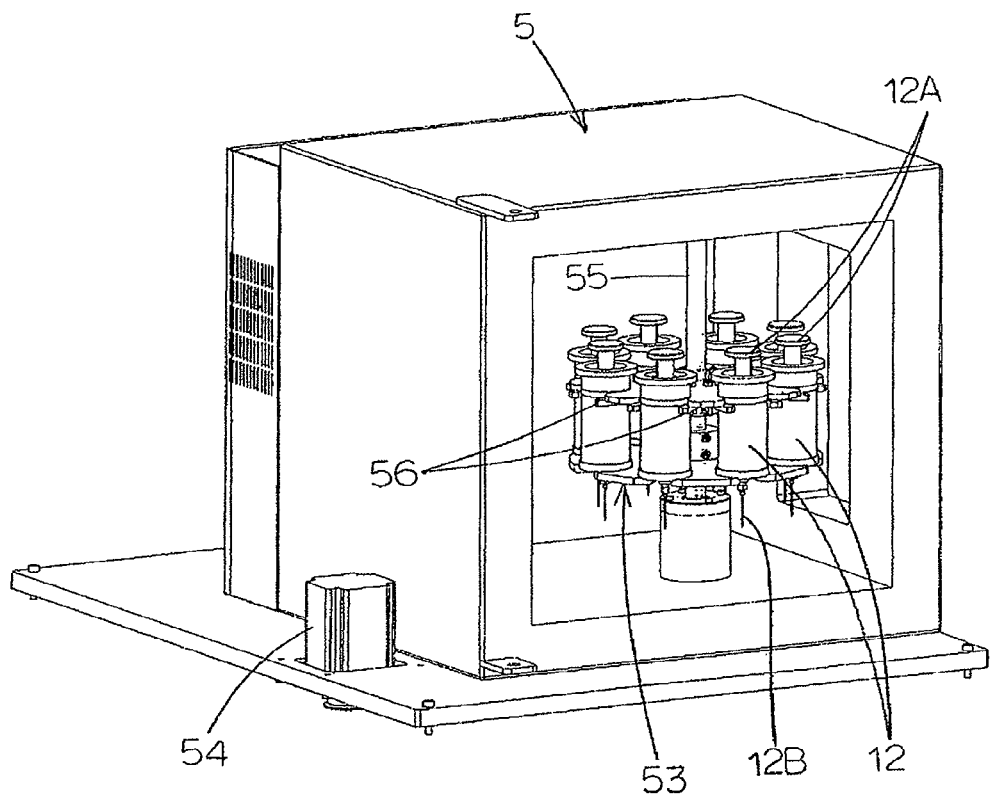

[Fig. 9]
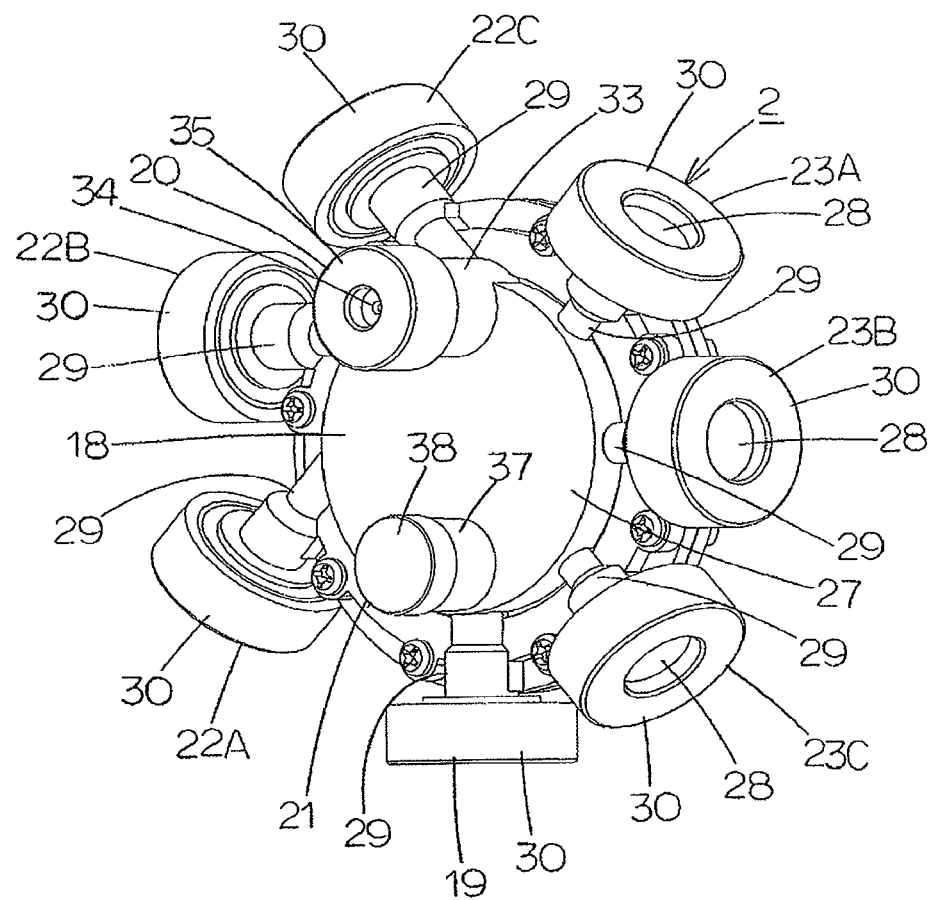

[Fig. 10]
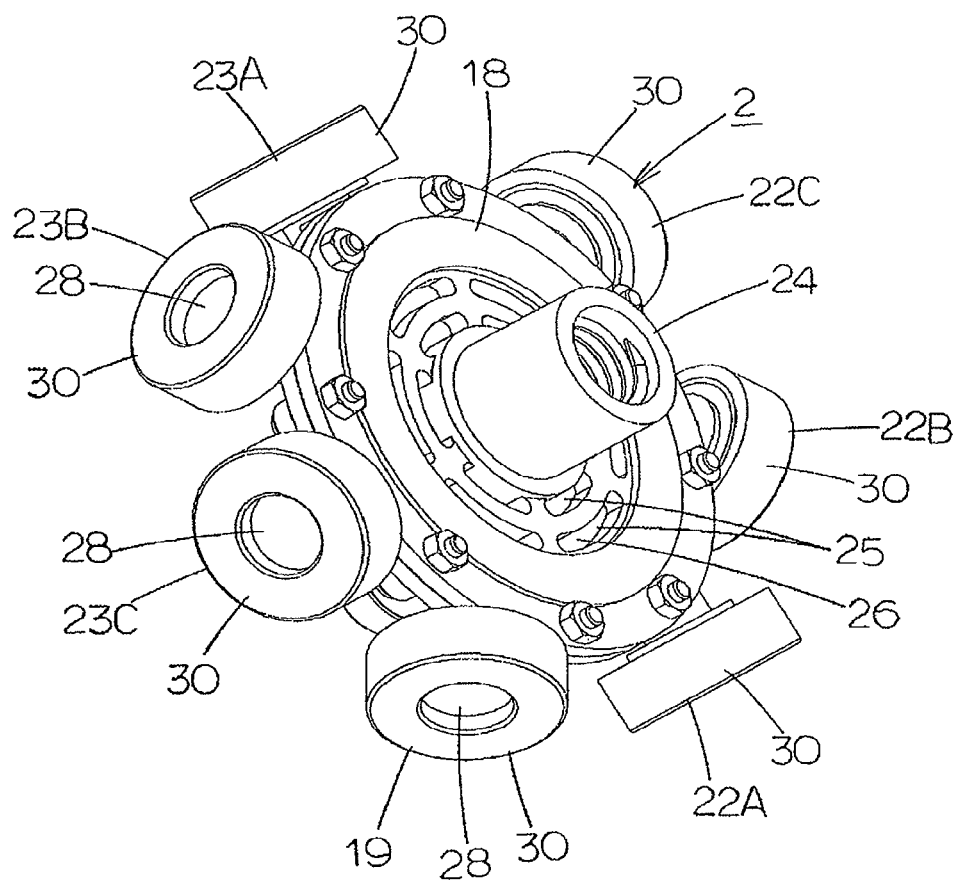

[Fig. 11]
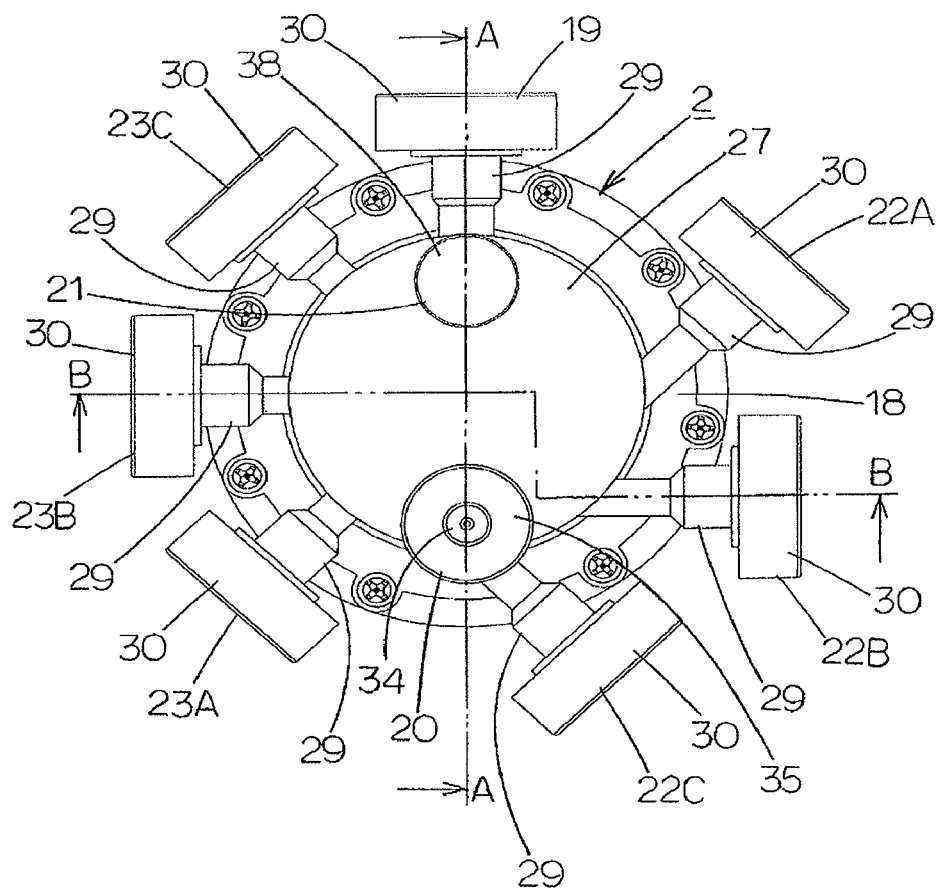

[Fig.12]
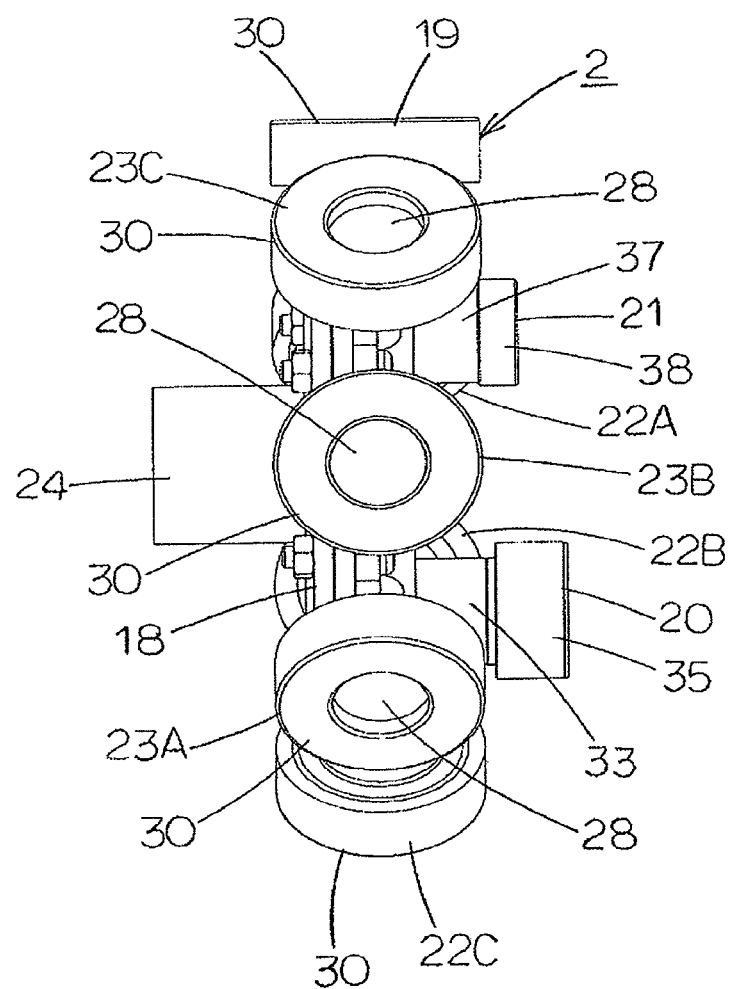

[Fig. 13]
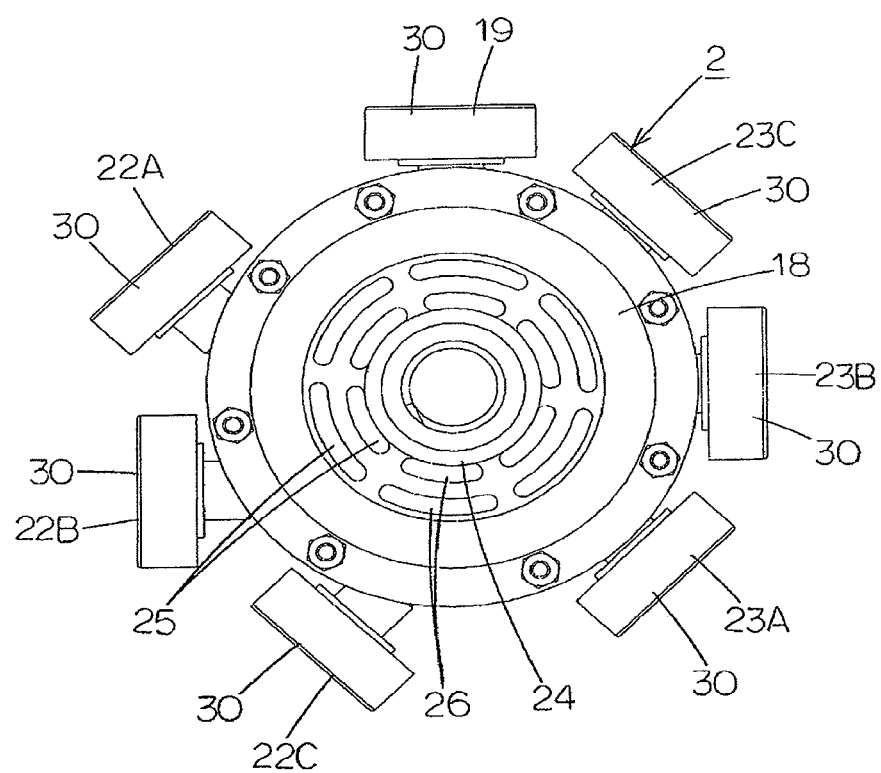

[Fig. 14]
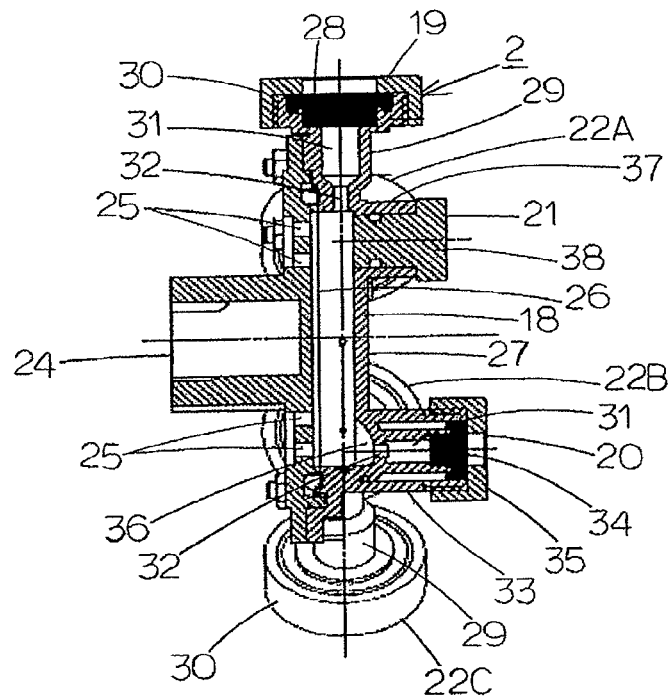
[Fig. 15]
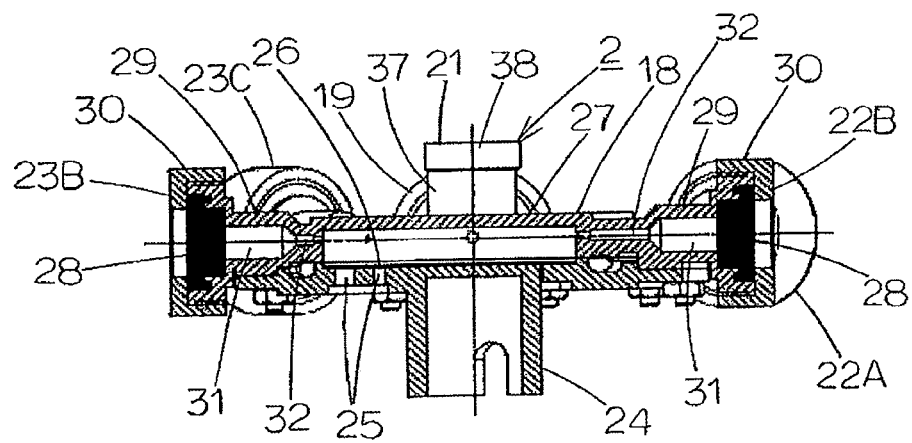

[Fig. 16]
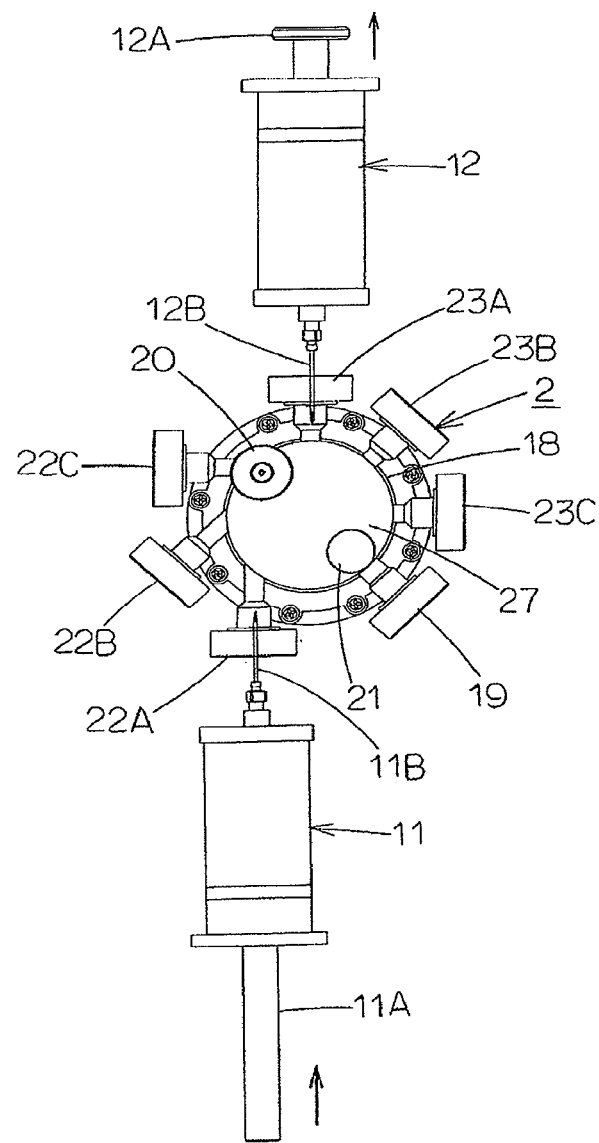

[Fig. 17]
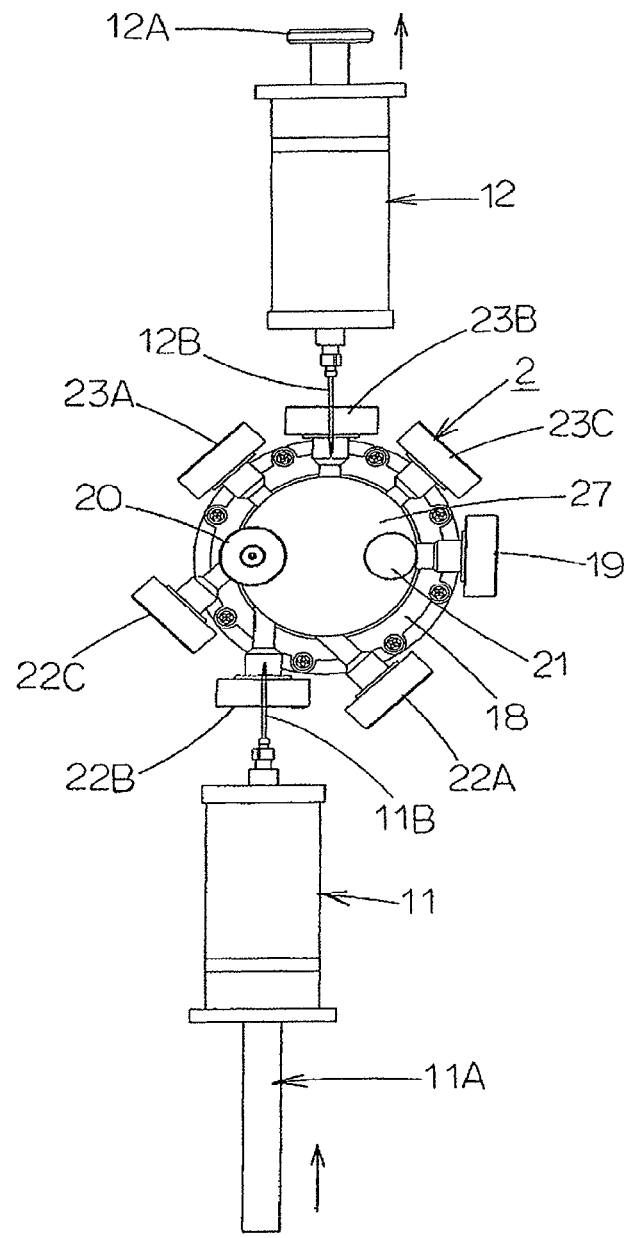

[Fig. 18]
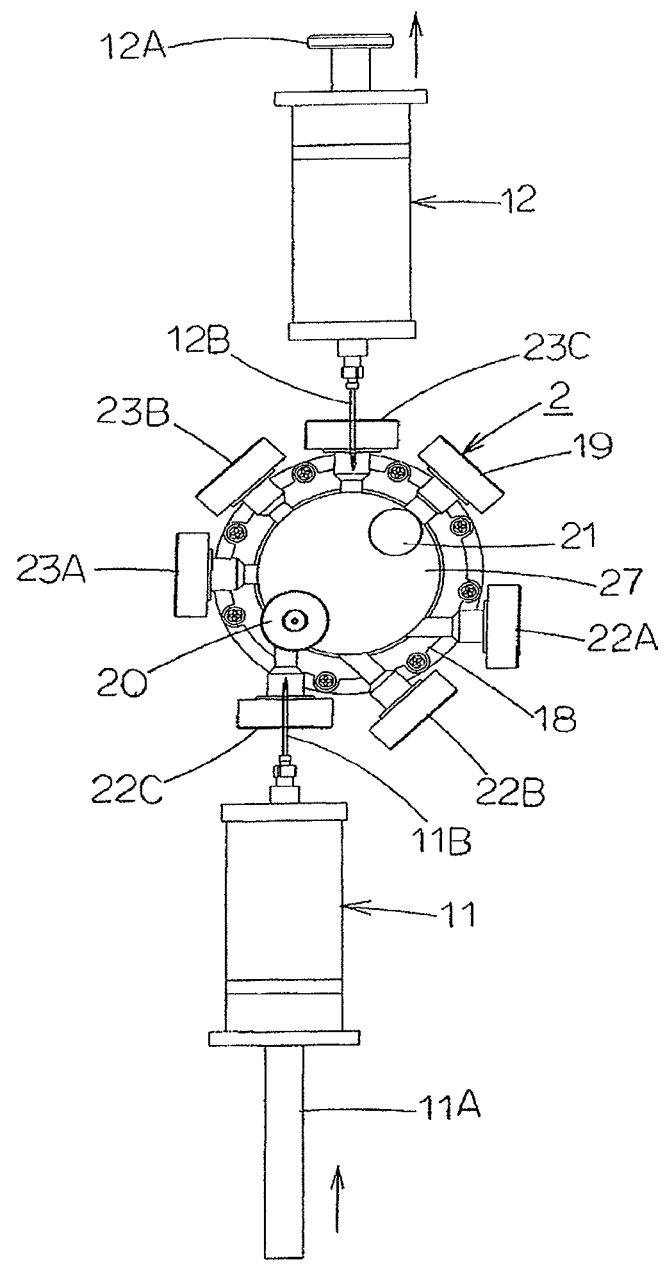

Automatic culture (Example)   Manual culture (Comparative Example)

[Fig. 21]
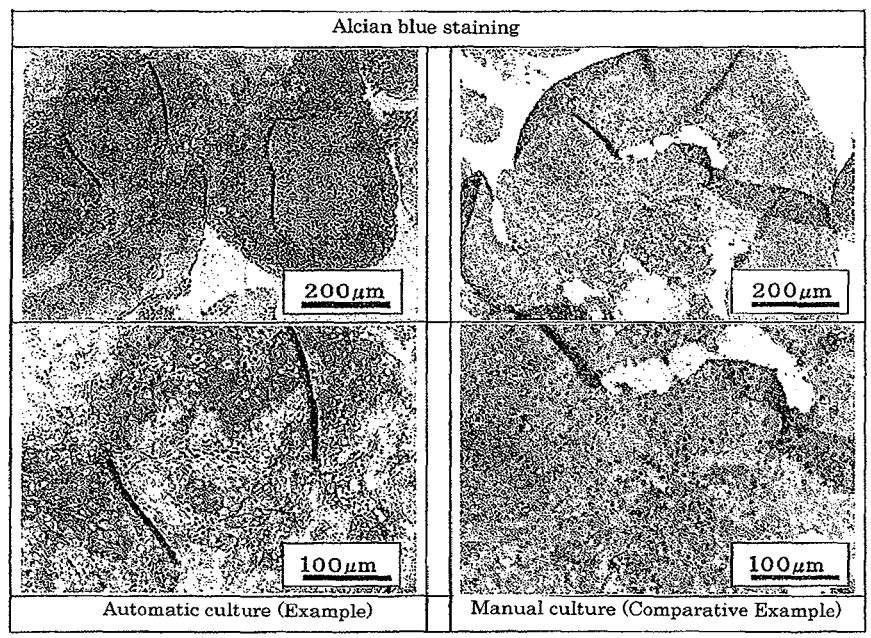
[Fig. 22]
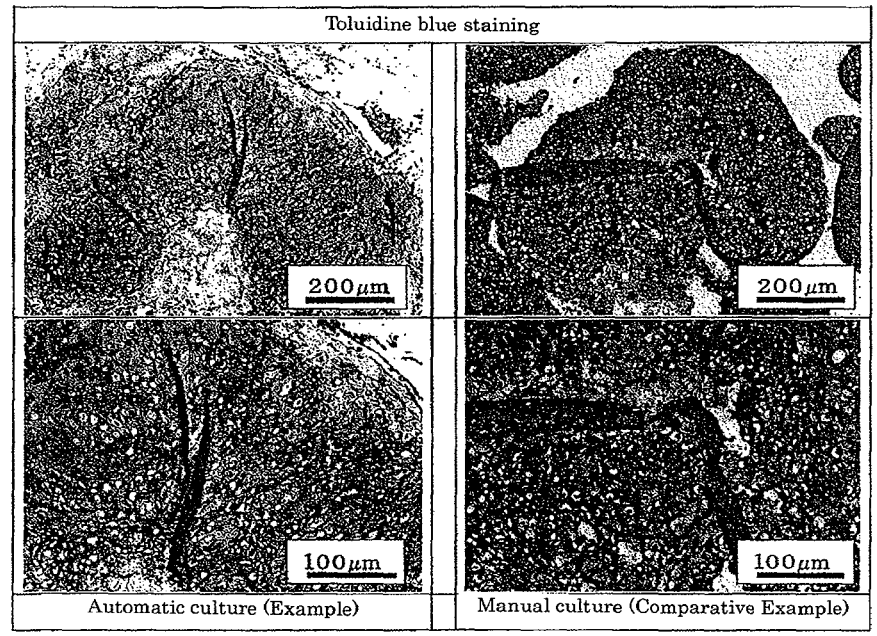

[Fig. 23]
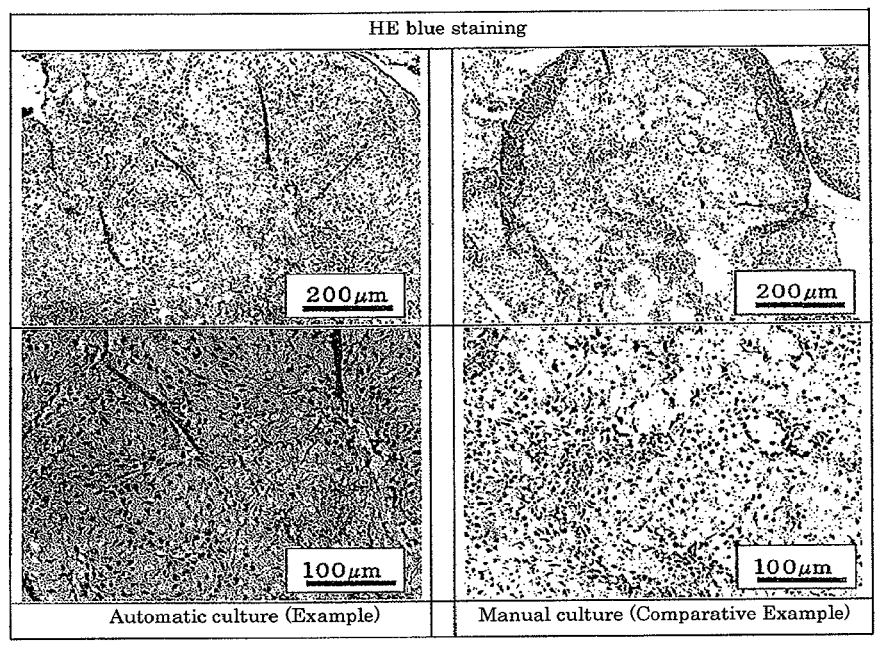

ROTATING CULTURE VESSEL AND AUTOMATIC CELL CULTURE APPARATUS USING SAME

CROSS REFERENCE TO RELATED APPLICATIONS

This application is a Divisional of U.S. patent application Ser. No. 13/375,606, filed Dec. 1, 2011, which is a PCT U.S. national stage application which claims priority of PCT/JP2010/059754, filed Jun. 9, 2010, which in turn claims priority to Japanese Patent Application No. 2009-138475, filed Jun. 9, 2009, which are all hereby incorporated herein by reference in their entireties.

TECHNICAL FIELD

The present invention relates to a rotating culture vessel and an automatic cell culture apparatus using the vessel, and more specifically relates to a rotating culture vessel suited for automatic exchange of a liquid culture medium and an automatic cell culture apparatus having an automatic liquid culture medium exchange function.

BACKGROUND ART

Conventionally, various automatic cell culture apparatuses have been supplied. For example, Patent Document 1 pertaining to a prior application of the present applicants discloses an automatic cell culture system. The automatic cell culture system can handle a plurality of culture cassettes containing a culture dish, automatically transfer the culture cassette with a robot arm for a dispensing operation and the like, control atmospheres such as gas concentration, temperature, and humidity in an incubator, and reliably prevent not only contamination in the incubator but also contamination during transfer of the culture dish for a dispensing operation and the like.

Patent Documents 2 and 3 also disclose an automatic cell culture apparatus that automates, for example, an exchange operation of a liquid culture medium with a general purpose multiple joints type robot in a two-dimensional culture apparatus. The automatic cell culture apparatus has an effect on the prevention of bacterial invasion by minimization of human intervention, but an expensive general purpose industrial robot performs the same operations as those that a human has performed, and such an apparatus requires high cost. Moreover, such an apparatus is not beyond common two-dimensional cell culture apparatuses and is not an apparatus for achieving three-dimensional culture.

Meanwhile, mesenchymal stem cells derived from the bone marrow has multipotency to be differentiated into tissues such as bone, cartilage, adipose, and ligament. However, it is known that, in a common in vitro culture, the cells are settled to the bottom of a petri dish due to the Earth's gravity to form a two-dimensional sheet and the original cell characteristics disappear. To address this, a culture method using a rotating wall vessel (RWV) bioreactor has been developed in order to achieve the three-dimensional culture in a microgravity environment that is nearly gravity-free, and cells are three-dimensionally cultured with appropriate differentiation inducing factors to be differentiated into an original tissue of the cell. A culture apparatus using the RWV is released from Synthecon. The apparatus is composed of a flat cylindrical vessel having a gas permeable membrane on the back side, and the vessel is rotated around an attaching part to which a horizontal rotating shaft of a rotation controller is attached. The rotation of the vessel constantly changes the gravity direction to cells, and consequently can generate a microgravity environment having one-hundredth the ground gravity by time average. Hence, clumps of cells are not settled and can be cultured while floating. The apparatus is typically referred to as a rotating culture device.

The RWV used in the conventional rotating culture device includes an inlet/outlet for a cell suspension and a pair of a supply port and a discharge port for a liquid culture medium on the front face orthogonal to the rotating shaft, and the liquid culture medium is exchanged manually. That is, for liquid culture medium exchange, the RWV is removed from the rotating shaft and left with the supply port and the discharge port facing upward, a rubber cap of the supply port is taken off, a leading end of a supply syringe including a new liquid culture medium is closely connected to the supply port, while a leading end of an empty discharge syringe is closely connected to the discharge port, then cocks of the supply port and the discharge port are unlocked, a piston of the supply syringe is pushed by one hand to supply the liquid culture medium into the vessel, and simultaneously a piston of the discharge syringe is pulled by the other hand to suck the used liquid culture medium in the vessel. The culture period of cells is typically about two weeks, and a culture medium is required to be exchanged every several days. Thus, the culture medium exchange operation that is complicated and requires a lot of skill must be carried out in each case. Such a manual culture medium exchange operation requires a lot of labor and time. When many RWVs are run, the exchange operation becomes a heavy burden as well as unexpected environmental contamination may occur during the culture medium exchange operation. In addition, the vessel having the cell suspension inlet, the supply port, and the discharge port on the front face has an disadvantage of small view for the observation of cells in the vessel.

To address this, the present applicant has developed an automatic cell culture apparatus as disclosed in Patent Document 4. Namely, the automatic cell culture apparatus includes a closed housing and a rotating culture device in the closed housing. The rotating culture device includes a cylindrical culture container having a horizontal rotating shaft, a cell suspension inlet, a supply port, and a discharge port, and each of the supply port and the discharge port has a septum seal structure for liquid culture medium exchange. The supply port and the discharge port are provided as a pair on the outer circumferential cylindrical face of the culture container at positions 180° apart from each other with respect to the rotating center toward the radial direction. The automatic cell culture apparatus also includes a syringe shifting means for inserting/withdrawing an injection needle of a supply syringe containing a new liquid culture medium to/from the supply port and for inserting/withdrawing an injection needle of an empty discharge syringe to/from the discharge port while locating the supply port and the discharge port on a vertical line with the supply port facing upward and includes a piston driving means for pushing a piston of the supply syringe while inserting the supply syringe into the supply port and for simultaneously pulling a piston of the discharge syringe while inserting the discharge syringe into the discharge port.

The apparatus thereby has a function of automatically exchanging a liquid culture medium in the rotating culture device using the RWV. Hence, such an apparatus can largely reduce burdens of culture operators such as researchers and achieve efficient cell culture as well as minimize the possibility of contamination in culture. When a plurality pairs of the supply ports and the discharge ports are provided on the outer circumferential cylindrical face of the culture container at an equal angle interval depending on a culture period and the number of liquid culture medium exchanges, the supply port and the discharge port can be newly used for every liquid culture medium exchange. Thus, such an apparatus has an advantage of minimizing the contamination during the liquid culture medium exchange.

CITATION LIST

Patent Literature

Patent Document 1: JP-A No. 2006-014675
Patent Document 2: JP-A No. 2006-115798
Patent Document 3: JP-A No. 2006-149268
Patent Document 4: JP-A No. 2008-237203

SUMMARY OF INVENTION

Technical Problem

However, the automatic cell culture apparatus disclosed in Patent Document 4 still has some problems. That is, air may not be completely substituted at the initial charging of a cell suspension to remain in the vessel, or air may be introduced into the vessel in culture through a permeable membrane on the backside. Accumulated gas in the vessel disturbs the flow of a liquid culture medium to provide irregular load to cells during rotation culturing, and hence air bleeding is essential. In conventional exchange of a liquid culture medium, a vessel is positioned with the supply port and the discharge port for a liquid culture medium in the vertical direction and with the supply port locating at the upper position, and a liquid culture medium is supplied with the supply syringe from the top and is sucked with the discharge syringe from the bottom. Hence, gas accumulated in the upper part of the vessel cannot be bled.

Therefore, in view of the above circumstances, it is an object of the present invention to provide a rotating culture vessel that can automate cell seeding, liquid culture medium exchange, quality control, and the like based on the rotation culture technique using the RWV and that can simultaneously bleed air during the liquid culture medium exchange without disturbing cultured cells and an automatic cell culture apparatus using the vessel.

Solution to Problem

In order to solve the above problems, the present invention provides a rotating culture vessel used for three-dimensional culture of a cell in a nearly gravity-free microgravity environment, the rotating culture vessel including a cell and a liquid culture medium and being attached to a horizontal rotating shaft of a rotating culture device. The rotating culture vessel is characterized by including one or more inlets/outlets for supplying a cell and a liquid culture medium at a initial stage and taking out a cultured cell at an appropriate position on a flat cylindrical culture container, and at least one pair of a supply port and a discharge port for liquid culture medium exchange on an outer circumferential cylindrical face of the culture container. The pair of the supply port and the discharge port are positioned 180° opposite to each other, the discharge port has a center line passing through a rotating center, and the supply port has a center line eccentrically positioned with respect to the rotating center.

It is more preferable that a distance between the center line of the supply port and the rotating center is 0.5r to 0.9r where the culture container has a culture space having a radius of r.

It is also preferable that three pairs of the supply ports and the discharge ports are provided on the outer circumferential cylindrical face of the culture container and the supply ports and the discharge ports are provided at an equal angle interval.

It is preferable that each of the supply port and the discharge port has a septum seal structure, a supply syringe used for liquid culture medium exchange has a leading end having an injection needle optionally passing through the septum seal, a discharge syringe used for liquid culture medium exchange has a leading end having an injection needle optionally passing through the septum seal, a new liquid culture medium is supplied from the supply syringe while a used liquid culture medium is sucked with the discharge syringe, and air is optionally bled with the discharge syringe.

The outer circumferential cylindrical face of the culture container includes a cell suspension supply port for supplying a cell suspension composed of a cell and a liquid culture medium, a front face orthogonal to the rotating shaft of the culture container includes an air bleeding port and a cell discharge port, each of the cell suspension supply port and the air bleeding port has a septum seal structure, and the cell discharge port has a rubber plug structure with a large opening.

Each port having the septum seal structure includes an inlet flow path having a large diameter for accepting the injection needle behind the septum seal and an orifice flow path having a small diameter between the inlet flow path and the culture space of the culture container.

The present invention also provides an automatic cell culture apparatus using the rotating culture vessel and used for three-dimensional culture of a cell in a nearly gravity-free microgravity environment. The automatic cell culture apparatus is characterized by including a closed housing having an air conditioning function, an incubator box of a rotating culture device in a middle chamber of the closed housing, a cool supply box storing a supply syringe for supplying a liquid culture medium in a lower chamber of the closed housing, and a cool discharge box storing a discharge syringe for collecting a liquid culture medium in an upper chamber of the closed housing. Each of the incubator box, the cool supply box, and the cool discharge box includes a front face having an automatically operated door. The rotating culture device has a shaft direction shifting means shifting a horizontal rotating shaft back and forth in a shaft direction, the horizontal rotating shaft is provided in the incubator box, and the rotating shaft has an end removably installed with the rotating culture vessel. A front space of the cool supply box includes an XYZ-axis shifting mechanism for supply, the XYZ-axis shifting mechanism for supply includes a movable part for supply driven by the mechanism, and the movable part for supply has a fixing chuck for holding the supply syringe upward and a push up means for pushing a piston up. A front space of the cool discharge box includes an XYZ-axis shifting mechanism for discharge, the XYZ-axis shifting mechanism for discharge includes a movable part for discharge driven by the mechanism, and the movable part for discharge has a fixing chuck for holding the discharge syringe downward and a pull up means for pulling a piston up. Each door is opened, the shaft direction shifting means is driven to bring the rotating culture vessel from the incubator box to a front space, and the rotating culture vessel is stopped with the supply port facing downward and the discharge port facing upward. The XYZ-axis shifting mechanism for supply and the fixing chuck are driven to take out the supply syringe from the cool supply box and to locate the supply syringe below the rotating culture vessel, and the XYZ-axis shifting mechanism for discharge and the fixing chuck are driven to take out the discharge syringe from the cool discharge box and to locate the discharge syringe above the rotating culture vessel. The XYZ-axis shifting mechanism for supply is driven to airtightly connect the supply syringe to the supply port, simultaneously the XYZ-axis shifting mechanism for discharge is driven to airtightly connect the discharge syringe to the discharge port, and then the push up means and the pull up means are synchronously driven to exchange a liquid culture medium in the rotating culture vessel.

Each of the cool supply box and the cool discharge box includes a rotating revolver type stacker and a plurality of holders around the stacker. The stacker has a vertical rotating shaft controlled with a stepping motor, and each holder elastically removably holds the syringe in a transverse direction with the syringe in the vertical direction.

It is preferable that the rotating culture device includes a plurality of the rotating shafts shifted back and forth by a common shaft direction shifting means, the rotating shafts are not overlapped in the vertical direction, ends of the rotating shafts are displaced back and forth, and the adjacent rotating culture vessels do not interfere with each other in the case of the rotating culture vessels being installed to the corresponding rotating shafts.

Advantageous Effects of Invention

The rotating culture vessel of the present invention as described above includes one or more inlets/outlets for supplying cells and a liquid culture medium at a initial stage and taking out cultured cells at an appropriate position on a flat cylindrical culture container and at least one pair of a supply port and a discharge port for liquid culture medium exchange on an outer circumferential cylindrical face of the culture container. The pair of the supply port and the discharge port are positioned 180° opposite to each other, the discharge port has a center line passing through a rotating center, and the supply port has a center line eccentrically positioned with respect to the rotating center. Hence, the rotating culture vessel is stopped with the supply port facing downward and the discharge port facing upward, the supply syringe including a new liquid culture medium is connected to the supply port, while the discharge syringe is connected to the discharge port, the piston of the supply syringe is pushed up to supply the new liquid culture medium into the culture container, and the piston of the discharge syringe is simultaneously pulled up to suck a used liquid culture medium for liquid culture medium exchange, as well as at the time, gas accumulated in the upper part of the culture container can be sucked with the discharge syringe. The center line of the supply port is eccentrically positioned with respect to the rotating center, hence, even when clumps of cells in culture are settled down to be placed in the lower part of the culture container, disassembling of the clumps of cells due to the flow caused by the supply of the liquid culture medium can be suppressed because the supply port is placed avoiding the clumps of cells. In particular, the effect is increased when the distance between the center line of the supply port and the rotating center is 0.5r to 0.9r where the culture container has a culture space having a radius of r. The culture container does not have a supply port and a discharge port interrupting the view on the front face, and thus the progress of culture is easily observed.

Three pairs of the supply ports and the discharge ports are provided on the outer circumferential cylindrical face of the culture container, and thus a liquid culture medium can be exchanged three times. Hence, the culturing can be continued for about two weeks that is a common cell culture period, and the supply port and the discharge port can be newly used for every exchange of a liquid culture medium. Therefore, the occurrence of contamination can be minimized. When the supply ports and the discharge ports are provided at an equal angle interval, the supply port and the discharge port can be readily located at exact positions.

When each of the supply port and the discharge port has a septum seal structure and each of the supply syringe and the discharge syringe used for liquid culture medium exchange has a leading end with an injection needle that can pass through the septum seal, the passing of the injection needle through the septum seal can achieve airtight connection, and a new liquid culture medium is supplied from the supply syringe while a used liquid culture medium is sucked with the discharge syringe as well as air can be bled with the discharge syringe. Furthermore, when the injection needle is removed from the septum seal, the hole formed with the injection needle is self-repaired to be closed. Thus, the supply port and the discharge port do not require a special structure for switching operation, and the supply port and the discharge port can be downsized. Therefore, the outer circumferential cylindrical face of the culture container can have three pairs of the supply ports and the discharge ports.

The outer circumferential cylindrical face of the culture container includes the cell suspension supply port for supplying a cell suspension composed of cells and a liquid culture medium, and a front face orthogonal to the rotating shaft of the culture container includes an air bleeding port and a cell discharge port. Hence, the culture container is kept in a horizontal position with the front face facing upward, a cell suspension supply syringe is connected to the cell suspension supply port, an air discharge syringe is connected to the air bleeding port, a cell suspension is supplied from the cell suspension supply syringe, air in the culture container is simultaneously sucked with the air discharge syringe, the air in the culture container is replaced with the cell suspension, and initial culture preparation can be completed. In particular, when each of the cell suspension supply port and the air bleeding port has the septum seal structure, an insertion of the injection needle of the syringe to the septum seal can simply achieve airtight connection to lead to easy manual operation. The cell discharge port has a rubber plug structure with a large opening, and hence clumps of cells can be readily taken out after culture.

Each port having the septum seal structure includes the inlet flow path having a large diameter for accepting the injection needle behind the septum seal and the orifice flow path having a small diameter between the inlet flow path and the culture space of the culture container. Thus, even when the injection needle is inserted into the septum seal at a slightly dislocated position, the injection needle can be accepted into the inlet flow path, and the supply syringe can supply a liquid culture medium through the orifice flow path into the culture space. Hence, such a structure can minimize the disturbance in the culture space due to the liquid culture medium flow and can suppress the introduction of air remaining in the inlet flow path through the orifice flow path into the culture space in rotation culture. Furthermore, the circumferential face of the culture space has a small hole of the orifice flow path alone, and thus the liquid culture medium is not disturbed in rotation culture.

The automatic cell culture apparatus of the present invention is based on the rotation culture technique using RWVs and has the function of automatic liquid culture medium exchange. Thus, such an apparatus can largely reduce burdens of culture operators such as researchers to achieve efficient cell culture as well as can minimize the possibility of contamination in culture. Hence, even medical institutions not having CPC in compliance with GMP can expect clinical application of regenerative medicine, and consequently, the regenerative medicine can be greatly generalized. The present invention can completely automate the liquid culture medium exchange operation that has been proven by conventional manual operation in which a new liquid culture medium is supplied into a culture container in a rotating culture vessel from a supply port with a supply syringe and a used liquid culture medium is simultaneously sucked from a discharge port with a discharge syringe. That is, the new liquid culture medium is supplied into the culture space of the rotating culture vessel from the supply port facing downward with the supply syringe, the used liquid culture medium is simultaneously sucked from the discharge port facing upward with the discharge syringe, and concurrently air can be bled. The center line of the supply port is eccentrically positioned with respect to the rotating center, and thus the disassembling of the clumps of cells can be suppressed as described above. The used liquid culture medium sucked in the discharge syringe is stored in the cool discharge box, and hence the contamination can be checked later.

Typically, each of the supply port and the discharge port is used only once for the liquid culture medium exchange, but the rotating culture vessel has a comparatively small culture space, for example, a small vessel has a volume of 10 ml and a large vessel has a volume of 20 ml. Thus, the numbers of the supply ports and the discharge ports are limited on the outer circumference. In the case of a long term culturing, each of the supply port and the discharge port may be used twice or more. In such a case, the numbers of the supply syringes and the discharge syringes require more than the number of the supply ports, but the use of a rotating revolver type stacker having a plurality of holders around the stacker can achieve the supply and the storage of the supply syringes and the discharge syringes.

Even in the case that each of the supply port and the discharge port is used once for the liquid culture medium exchange, when the rotating culture device includes a plurality of rotating shafts, a plurality of rotating culture vessels are installed to the ends, and a plurality of cell lines are simultaneously cultured, it is required that the numbers of the supply syringes and the discharge syringes, obtained by multiplying the number of the vessels by the number of pairs of the supply ports and the discharge ports. In such a case, the rotating revolver type stacker having a plurality of holders around the stacker can be used.

BRIEF DESCRIPTION OF THE DRAWINGS

FIG. 1 is a general perspective view of an automatic cell culture apparatus of the present invention except for a part of an outer cover.

FIG. 2 is a side view showing the internal structure of the automatic cell culture apparatus of the present invention.

FIG. 3 is an elevation view showing the internal structure of the automatic cell culture apparatus of the present invention.

FIG. 4 is a perspective view showing a mechanism part of a rotating culture device having a shaft direction shifting means.

FIG. 5 is a perspective view showing a XYZ-axis shifting mechanism for supply.

FIG. 6 is a perspective view showing a XYZ-axis shifting mechanism for discharge.

FIG. 7 is a perspective view of a cool supply box having a rotating revolver type stacker.

FIG. 8 is a perspective view of a cool discharge box having the rotating revolver type stacker.

FIG. 9 is a perspective view of a rotating culture vessel of the present invention viewed from the front side.

FIG. 10 is a perspective view of the rotating culture vessel of the present invention viewed from the back side.

FIG. 11 is an elevation view of the rotating culture vessel.

FIG. 12 is a left side view of the rotating culture vessel.

FIG. 13 is a back view of the rotating culture vessel.

FIG. 14 is a cross-sectional view taken along the line A-A in FIG. 11.

FIG. 15 is a cross-sectional view taken along the line B-B in FIG. 11.

FIG. 16 is a schematic diagram showing the liquid culture medium exchange operation using the first pair of the supply port and the discharge port.

FIG. 17 is a schematic diagram showing the liquid culture medium exchange operation using the second pair of the supply port and the discharge port.

FIG. 18 is a schematic diagram showing the liquid culture medium exchange operation using the third pair of the supply port and the discharge port.

FIG. 21 are micrographs of cartilage tissues stained with Alcian blue.

FIG. 22 are micrographs of cartilage tissues stained with toluidine blue.

FIG. 23 are micrographs of cartilage tissues stained with HE.

DESCRIPTION OF EMBODIMENTS

Figure 19:
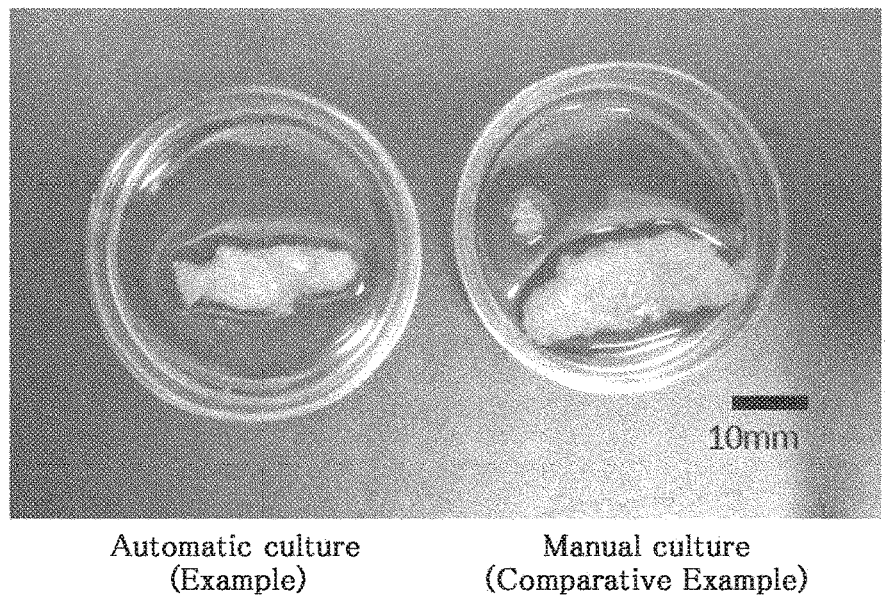
FIG. 19 is a photograph in place of a drawing, showing external appearances of cartilage tissues as the results of cartilage tissue formation experiment using bone marrow cells of Japanese white rabbits using the automatic cell culture apparatus of the present invention (automatic culture) and a conventional rotating culture device (manual culture).

Next, the present invention will be described in further detail based on embodiments shown in attached drawings. FIG. 1 to FIG. 8 show the automatic cell culture apparatus of the present invention, and FIG. 9 to FIG. 15 show the rotating culture vessel of the present invention. In Figures, the sign 1 represents the automatic cell culture apparatus, the sign 2 represents the rotating culture vessel, the sign 3 represents a rotating culture device, the sign 4 represents a cool supply box, the sign 5 represents a cool discharge box, the sign 6 represents a shaft direction shifting means, the sign 7 represents an XYZ-axis shifting mechanism for supply, and the sign 8 represents an XYZ-axis shifting mechanism for discharge.

The automatic cell culture apparatus 1 of the present invention uses a rotating culture vessel 2 and is used for three-dimensional culture of cells in a microgravity environment that is nearly gravity-free. The automatic cell culture apparatus includes a closed housing 9 having an air conditioning function, the closed housing 9 includes a middle chamber that includes a rotating culture device 3 having an incubator box 10 in which one or more rotating culture vessels 2 are installed for culture, a lower chamber that includes a cool supply box 4 storing a supply syringe 11 for supplying a liquid culture medium, and an upper chamber that includes a cool discharge box 5 storing a discharge syringe 12 for collecting a liquid culture medium. Each of the incubator box 10, the cool supply box 4, and the cool discharge box 5 includes a front face having an automatically operated door (not shown in the drawings). The rotating culture device 3 has a shaft direction shifting means 6 shifting a horizontal rotating shaft 13 provided in the incubator box 10 back and forth in the shaft direction, and the rotating shaft 13 has an end that is removably installed with the rotating culture vessel 2. A front space of the cool supply box 4 includes an XYZ-axis shifting mechanism 7 for supply, the XYZ-axis shifting mechanism 7 for supply includes a movable part for supply driven by the mechanism, and the movable part for supply has a fixing chuck 14 for holding the supply syringe 11 upward and a push up means 15 for pushing a piston 11A up. A front space of the cool discharge box 5 includes an XYZ-axis shifting mechanism 8 for discharge, the XYZ-axis shifting mechanism 8 for discharge includes a movable part for discharge driven by the mechanism, and the movable part for discharge has a fixing chuck 16 for holding the discharge syringe 12 downward and a pull up means 17 for pulling a piston 12A up. In the present embodiment, the shaft direction of the rotating shaft 13 is regarded as an X axis, the horizontal direction orthogonal to the X axis is regarded as a Y axis, and the vertical direction is regarded as a Z axis for description.

In the present embodiment, a plurality of rotating shafts 13 that are shifted back and forth in the X axis direction by a common shaft direction shifting means 6 are provided while the rotating shafts are not overlapped in the vertical direction. Ends of the rotating shafts 13 are displaced back and forth so that the adjacent rotating culture vessels 2 will not interfere with each other when the rotating culture vessels 2 are installed to the corresponding rotating shafts 13. In the present embodiment, two rotating shafts 13 are provided in parallel to achieve cell culture using two rotating culture vessels 2 at the same time.

Next, the rotating culture vessel 2 will be described in detail based on FIG. 9 to FIG. 15. The rotating culture vessel 2 includes a cell suspension supply port 19 for supplying a cell suspension composed of cells and a liquid culture medium on an outer circumferential cylindrical face of a flat cylindrical culture container 18 as well as includes an air bleeding port 20 and a cell discharge port 21 on a front face orthogonal to the rotating shaft 13 of the culture container 18. The rotating culture vessel 2 further includes at least one pair of a supply port 22 and a discharge port 23 for liquid culture medium exchange on the outer circumferential cylindrical face of the culture container 18. The pair of the supply port 22 and the discharge port 23 is positioned 180° opposite to each other, the discharge port 23 has a center line passing through the rotating center, and the supply port 22 has a center line eccentrically positioned with respect to the rotating center.

In the present embodiment, three pairs of the supply ports 22 and the discharge ports 23 are provided on the outer circumferential cylindrical face of the culture container 18, and these ports will be distinguished by A, B, and C. The supply ports 22A, 22B, and 22C are provided at an equal angle interval and the discharge ports 23A, 23B, and 23C are also provided at an equal angle interval. In the present embodiment, the cell suspension supply port 19 and the cell discharge port 21 are independently provided, but one port may be provided to serve as both ports. Here, the distance between the center line of the supply port 22 and the rotating center is 0.5r to 0.9r where the culture container 18 has a culture space having a radius of r.

The rotating culture vessel 2 further includes, at the back center, a protruding attaching part 24 that is removably installed to the end of the rotating shaft 13 in the rotating culture device 3. The attaching part 24 has a structure so that the vessel will be attached at the same rotational position with respect to the end of the rotating shaft 13 at any time. The rotating culture vessel 2 of the embodiment is expected to have a volume of 10 to 20 ml because a liquid culture medium is expensive, but the volume should be determined depending on the size of clumps of cells to be cultured.

As shown in FIG. 10, FIG. 13, FIG. 14, and FIG. 15, the rotating culture vessel 2 has air intake ports 25 on the back side around the attaching part 24, and a gas permeable membrane 26 is provided inside the air intake port 25. Through the membrane, oxygen can be supplied into a liquid culture medium while carbon dioxide can be discharged. The rotating culture vessel 2 also has an observation window 27 on the front side so that the inside can be observed.

As shown in FIG. 15, each of the supply port 22 and the discharge port 23 has a septum seal structure. The supply syringe 11 and the discharge syringe 12 used for liquid culture medium exchange have injection needles 11B and 12B, respectively, at the leading ends, and each injection needle can pass through the septum seal 28. The supply port 22 is positioned downward, and the discharge port 23 is positioned upward. A new liquid culture medium is supplied from the lower side with the supply syringe 11 while a used liquid culture medium is sucked from the upper side with the discharge syringe 12 and air can be bled with the discharge syringe 12. Each of the supply port 22 and the discharge port 23 has the septum seal structure, and thus the injection needles 11B and 12B installed to the leading ends of the supply syringe 11 and the discharge syringe 12 pass through the septum seals 28 to achieve airtight connection. Moreover, even when the injection needles 11B and 12B are removed, the through holes are closed due to elastic recovery of the septum seal to maintain the airtight condition.

More specifically, the supply port 22 and the discharge port 23 have the same cross sectional structure as shown in FIG. 15. The supply port 22 includes a port 29 that is eccentrically positioned with respect to the rotating center of the outer circumferential cylindrical face of the culture container 18 and continues to the culture space. The supply port 22 further includes a silicon rubber septum seal 28 in an end part of the port 29. The circumference of the septum seal 28 is pressed with a pressing cap 30 screwed with the port 29 to lead to a closed structure. Meanwhile, the discharge port 23 includes a port 29 that continues to the culture space toward the radial direction passing through the rotating center of the outer circumferential cylindrical face of the culture container 18. The discharge port 23 further includes a silicon rubber septum seal 28 in an end part of the port 29. The circumference of the septum seal 28 is pressed with a pressing cap 30 screwed with the port 29 to lead to a closed structure. Each port 29 constituting the supply port 22 and the discharge port 23 having the septum seal structures includes an inlet flow path 31 having a large diameter behind the septum seal 28 and an orifice flow path 32 having a small diameter between the inlet flow path 31 and the culture space in the culture container 18, and the inlet flow path 31 accepts the injection needle 11B or 12B.

The leading end of the injection needle 11B of the supply syringe 11 passed thorough the septum seal 28 of the supply port 22 is accepted in the inlet flow path 31 in the port 29, and thus even when the injection needle 11B is inserted into the septum seal 28 slightly dislocated from the center, the leading end of the injection needle 11B does not come in contact with the port 29 to be used without problems. Hence, request to the positioning precision of the XYZ-axis shifting mechanism 7 for supply is lowered, and the mechanism can be formed using a cheap actuator. The orifice flow path 32 is also provided. Thus, a liquid culture medium supplied in the inlet flow path 31 is introduced through the orifice flow path 32 having a small diameter into the culture space, and the disturbance generated in the culture space can be minimized. The leading end of the injection needle 12B of the discharge syringe 12 passed through the septum seal 28 of the discharge port 23 is also accepted in the inlet flow path 31 in the port 29, and a used liquid culture medium and air accumulated in the culture space can be discharged through the orifice flow path 32 by suction. Even when air is accumulated in the inlet flow path 31, the air does not flow into the culture space through the orifice flow path 32 in rotation culture due to the surface tension of an liquid culture medium.

As shown in FIG. 14, each of the cell suspension supply port 19 and the air bleeding port 20 has a septum seal structure similar to the above, and the cell discharge port 21 has a rubber plug structure having a large opening. That is, as with the discharge port 23, the cell suspension supply port 19 includes a port 29 that continues to the culture space toward the radial direction passing through the rotating center. The cell suspension supply port 19 also includes a silicon rubber septum seal 28 in an end part of the port 29. The circumference of the septum seal 28 is pressed with a pressing cap 30 screwed with the port 29 to lead to a closed structure. The air bleeding port 20 and the cell discharge port 21 are positioned on the periphery of the front face of the culture container 18 opposite to each other with respect to the rotating center. The air bleeding port 20 includes a port 33 protruded from the front face of the culture container 18 and a silicon rubber septum seal 34 in an end part of the port 33. The circumference of the septum seal 34 is pressed with a pressing cap 35 screwed with the port 33 to lead to a closed structure. Each of the port 29 of the cell suspension supply port 19 and the port 33 of the air bleeding port 20 includes an inlet flow path 31 and an orifice flow path 32 in a similar manner to the above. An inside where the orifice flow path 32 of the air bleeding port 20 is opened toward the culture space has a concave part 36 in which air in the culture space is accumulated when the rotating culture vessel 2 is horizontalized. The cell discharge port 21 includes a port 37 having a large inner diameter, and the port is tightly fitted with a rubber plug 38. The rubber plug 38 has a leading end face that is flush with the inner wall of the culture space so as not to disturb a liquid culture medium in rotation culture.

In order to supply cells and a liquid culture medium into the rotating culture vessel 2, the rotating culture vessel 2 is left with the observation window 27 facing upward and the rotating shaft in the vertical direction, an injection needle of a cell suspension supply syringe (not shown in the drawings) containing the cells and the liquid culture medium is inserted into the septum seal 28 of the cell suspension supply port 19, an injection needle of an empty air bleeding syringe (not shown in the drawings) is inserted into the septum seal 34 of the air bleeding port 20, and the cell suspension is supplied from the cell suspension supply syringe into the culture space while air is bled with the air bleeding syringe. At the time, the air in the culture space is finally accumulated in the concave part 36, and the air accumulated in the concave part 36 is discharged from the culture space.

Next, the automatic cell culture apparatus 1 for culturing cells while automatically exchanging a liquid culture medium using the rotating culture vessel 2 will be described in detail based on FIG. 1 to FIG. 8 and FIG. 16 to FIG. 18. As shown in FIG. 1, the closed housing 9 has opening and closing doors on the front face and one side face. The front face has three inspection doors 39 corresponding to the rotating culture device 3, the cool supply box 4, and the cool discharge box 5. The closed housing 9 has a transparent front panel so that the inside can be observed. The closed housing 9 includes the side face having one operation door 40 for the preparation of a series of culture or for the treatment after culture. That is, the operation door 40 is opened, the rotating culture vessel 2 is attached to or removed from the rotating shaft 13, the supply syringes 11 are attached to or removed from the inside of the cool supply box 4, and the discharge syringes 12 are attached to or removed from the inside of the cool discharge box 5. The operation door 40 is transparent so that the inside can be observed. The closed housing 9 includes a ceiling having an air conditioner 41 with filter function for keeping the inside at suitable temperature and for air cleaning.

As shown in FIG. 1 to FIG. 4, the rotating culture device 3 includes the incubator box 10 in which the temperature can be controlled and that contains a horizontal rotating shaft 13 as well as includes a rotation control mechanism 42 behind the incubator box, for driving the rotating shaft 13 at a predetermined rotation speed, and a shaft direction shifting means 6 for shifting the rotating shaft 13 together with the rotation control mechanism 42 back and forth in the shaft direction. The incubator box 10 has an automatically operated door on the front face and a manually operated door 43 on the side face having the operation door 40. In the present embodiment, two rotating shafts 13 are arranged in parallel in a horizontal position, and each rotating shaft is supported with a cylindrical shaft bearing 44 rotatably and slidably in the shaft direction. The shaft direction shifting means 6 has a structure to shift a movable part 46 in front and back directions along a linear guide 45 provided behind the incubator box 10. Ends of the rotating shafts 13 continuing backward from the back face of the incubator box 10 are interlocked by a rotation control mechanism 42 that is attached to the movable part 46 of the shaft direction shifting means 6 through a timing belt. There are two independent rotation control mechanisms 42 so as to independently control each rotation of the rotating shafts 13. The rotation control mechanism 42 is driven by a stepping motor or a servomotor so as to accurately control the rotation speed and the rotational position and controls the rotational position by, for example, reading a marker fixed on the rotating shaft 13 with a sensor. The leading end positions of the rotating shafts 13 are displaced back and forth as described above, and the rotating culture vessel 2 filled with a cell suspension is manually attached to or removed from each leading end.

As shown in FIG. 1 to FIG. 3 and FIG. 7, the cool supply box 4 includes an automatically operated door on the front face of the box in which temperature can be controlled, a manually operated door 47 on the side face having the operation door 40, and a rotating revolver type stacker 48 in the cool supply box. The stacker 48 includes a vertical rotating shaft 50 that is controlled with a stepping motor 49 and a plurality of holders 51 around the stacker 48. The holder 51 elastically removably holds the supply syringe 11 in a transverse direction with the injection needle 11B facing upward in the vertical direction. The holder 51 of the stacker 48 include an U-groove that accepts and locks the upper and lower parts of the supply syringe 11 and a grip that elastically grips the supply syringe 11 from both sides for holding. The supply syringe 11 is laterally pushed to be automatically held with the holder, and the supply syringe 11 is grasped and laterally pulled from the holder to be readily removed.

As shown in FIG. 1 to FIG. 3 and FIG. 8, the cool discharge box 5 has approximately the same structure as that of the cool supply box 4, and includes an automatically operated door on the front face of the box in which temperature can be controlled, a manually operated door 52 on the side face having the operation door 40, and a rotating revolver type stacker 53 in the cool discharge box 5. The stacker 53 includes a vertical rotating shaft 55 that is controlled with a stepping motor 54 and a plurality of holders 56 around the stacker 53. The holder elastically removably holds the discharge syringe 12 in a transverse direction with the injection needle 12B facing downward in the vertical direction. The stacker 53 has approximately the same structure as that of the stacker 48.

Next, the XYZ-axis shifting mechanism 7 for supply for transferring the supply syringe 11 will be described based on FIG. 2, FIG. 3, and FIG. 5. The XYZ-axis shifting mechanism 7 for supply is provided in a front space of the cool supply box 4 in the closed housing 9. The XYZ-axis shifting mechanism 7 for supply includes a Y-axis shifting mechanism 57 fixed to the bottom in the closed housing 9, a Z-axis shifting mechanism 58 fixed to a movable part of the Y-axis shifting mechanism 57, and an X-axis shifting mechanism 59 fixed to a movable part of the Z-axis shifting mechanism 58. The X-axis shifting mechanism 59 includes a movable part having a fixing chuck 14 for holding the supply syringe 11 upward and having a push up means 15 for pushing a piston 11A up. Each of the Y-axis shifting mechanism 57, the Z-axis shifting mechanism 58, and the X-axis shifting mechanism 59 is composed of a linear guide and a stepping motor driven with a ball screw, but the structure is not specifically limited. The fixing chuck 14 is composed of a U-groove plate 60 that locks a flange part of a cylinder of the supply syringe 11 and an air-driven hand 61 that grips the side face of the cylinder. The push up means 15 includes a protruded push up plate 63 that is provided on a movable part of a Z-axis shifting mechanism 62 and that is in contact with the lower end of the piston 11A. The movable part of the Z-axis shifting mechanism 62 along with the fixing chuck 14 are fixed to the movable part of the X-axis shifting mechanism 59.

Finally, the XYZ-axis shifting mechanism 8 for discharge for transferring the discharge syringe 12 will be described based on FIG. 2, FIG. 3, and FIG. 6. The XYZ-axis shifting mechanism 8 for discharge is provided in a front space of the cool discharge box 5 in the closed housing 9. The XYZ-axis shifting mechanism 8 for discharge includes a Y-axis shifting mechanism 64 fixed to an anterior top area in the closed housing 9, a Z-axis shifting mechanism 65 fixed to a movable part of the Y-axis shifting mechanism 64, and an X-axis shifting mechanism 66 fixed to a movable part of the Z-axis shifting mechanism 65. The X-axis shifting mechanism 66 includes a movable part having a fixing chuck 16 for holding the discharge syringe 12 downward and a pull up means 17 for pulling a piston 12A up. The fixing chuck 16 is composed of a U-groove plate 67 that locks a flange part of a cylinder of the discharge syringe 12 and an air-driven hand 68 that grips the side face of the cylinder. The pull up means 17 include a protruded pull up plate 70 that is provided on a movable part of a Z-axis shifting mechanism 69 and that locks a flange part at the upper end of the piston 12A for pulling up. The movable part of the Z-axis shifting mechanism 69 along with the fixing chuck 16 are fixed to the movable part of the X-axis shifting mechanism 66.

The procedure for culturing cells using the automatic cell culture apparatus 1 of the present invention will be described below. First, the operation door 40 of the closed housing 9 is opened, the door 47 of the cool supply box 4 is opened, a predetermined number of supply syringes 11 are installed to the stacker 48, and the door 47 is closed. The door 52 of the cool discharge box 5 is opened, an equal number of the discharge syringes 12 to that of the supply syringes 11 are installed to the stacker 53, and the door 52 is closed. Meanwhile, the door 43 of the incubator box 10 of the rotating culture device 3 is opened, the attaching part 24 of the rotating culture vessel 2 filled with a cell suspension is installed to the end of the rotating shaft 13, and the door 43 is closed. At the time, the rotating culture vessel 2 is fixed to a precise rotational position with respect to the rotating shaft 13 at any time. Next, the operation door 40 is closed, and the temperature in the closed housing 9 together with the incubator box 10 is kept at a predetermined temperature. This prevents that the temperature in the incubator box 10 is steeply changed to change a culture condition when the automatically operated door on the front face of the incubator box 10 is opened for liquid culture medium exchange. Each temperature in the cool supply box 4 and the cool discharge box 5 is controlled to be lower than the temperature in the incubator box 10 in order to store a new liquid culture medium before use and a used liquid culture medium without varying the condition.

Then, the rotation control mechanism 42 is driven to rotate the rotating culture vessel 2 at a predetermined rotation speed for cell culture. After culturing for a predetermined period of time, the rotation control mechanism 42 is controlled to stop the rotating culture vessel 2 with the first supply port 22A facing downward in the vertical direction and the first discharge port 23A facing upward in the vertical direction. Next, the automatically operated door on the front face of the incubator box 10 is opened, the shaft direction shifting means 6 is driven to shift the rotating culture vessel 2 forward, and the rotating culture vessel 2 is located in a front space of the incubator box 10. Simultaneously or before or after that, each automatically operated door on the front faces of the cool supply box 4 and the cool discharge box 5 is opened, each of the XYZ-axis shifting mechanism 7 for supply and the XYZ-axis shifting mechanism 8 for discharge is independently driven, the fixing chuck 14 is transferred into the cool supply box 4, the supply syringe 11 stored in the stacker 48 at a predetermined rotational position is held with the fixing chuck 14, then the supply syringe 11 is transferred into a front space of the cool supply box 4, as well as the fixing chuck 16 is transferred into the cool discharge box 5, the discharge syringe 12 stored in the stacker 53 at a predetermined rotational position is held with the fixing chuck 16, and then the discharge syringe 12 is transferred into a front space of the cool discharge box 5.

Next, the supply syringe 11 is located directly below the first supply port 22A of the rotating culture vessel 2, while the discharge syringe 12 is located directly above the discharge port 23A. Then, as shown in FIG. 16, the Z-axis shifting mechanism 58 of the XYZ-axis shifting mechanism 7 for supply and the Z-axis shifting mechanism 65 of the XYZ-axis shifting mechanism 8 for discharge are synchronously driven, the injection needle 11B of the supply syringe 11 is passed through the septum seal 28 of the supply port 22A for connection, and simultaneously, the injection needle 12B of the discharge syringe 12 is passed through the septum seal 28 of the discharge port 23A for connection. While maintaining this condition, the push up plate 63 of the push up means 15 is elevated to push the piston 11A of the supply syringe 11 up, a new liquid culture medium is supplied into the culture space of the rotating culture vessel 2, simultaneously, the pull up plate 70 of the pull up means 17 is elevated to pull the piston 12A of the discharge syringe 12 up, a used liquid culture medium is sucked out from the culture space of rotating culture vessel 2, and at the time, air accumulated in the culture space during culturing is also simultaneously sucked out. After the liquid culture medium in the rotating culture vessel 2 is exchanged in this manner, the Z-axis shifting mechanism 58 of the XYZ-axis shifting mechanism 7 for supply and the Z-axis shifting mechanism 65 of the XYZ-axis shifting mechanism 8 for discharge are synchronously driven, the injection needle 11B of the supply syringe 11 is removed from the supply port 22A, and simultaneously, the injection needle 12B of the discharge syringe 12 is removed from the discharge port 23A. Next, the XYZ-axis shifting mechanism 7 for supply and the XYZ-axis shifting mechanism 8 for discharge are driven, the used supply syringe 11 and the used discharge syringe 12 are installed in the original positions in the stacker 48 and the stacker 53, respectively, the fixing chuck 14 and the fixing chuck 16 are unlocked and returned from the cool supply box 4 and the cool discharge box 5 to stay at the initial positions. Meanwhile, the shaft direction shifting means 6 is driven to store the rotating culture vessel 2 in the incubator box 10, each automatically operated door is closed, and then the rotation control mechanism 42 is driven to rotate the rotating culture vessel 2 at a predetermined rotation speed for cell culture.

The liquid culture medium exchange operation is performed using a pair of the supply port 22B and the discharge port 23B of the rotating culture vessel 2 as shown in FIG. 17, and then the operation is repeated using a pair of the supply port 22C and the discharge port 23C as shown in FIG. 18. In this case, each of the stacker 48 and the stacker 53 is rotated by a predetermined angle so that a new supply syringe 11 and a new discharge syringe 12 will be located at the front in sequence.

The rotating culture device 3 employed in the present invention can keep cells in suspension without settling in the rotating culture vessel 2. Therefore, the rotating culture device 3 has advantages that three-dimensional aggregates can be formed, necrosis due to stirring stress can be avoided, differentiation inducers effectively work, and removal of waste products and supply of nutrients can be performed. In the present invention, a liquid culture medium can be sequentially supplied using a plurality of the supply syringes 11. Hence, a liquid culture medium having an optimum composition may be used depending on a culture stage of cells.

It is important to observe a culture condition in culture. The observation of the culture condition is carried out on, for example, (1) pH change and color change of a culture medium due to the consumption of culture medium additives, accumulation of waste products, and the like in culture, (2) presence or absence of turbidity of a culture medium due to contamination, and (3) whether a three-dimensional tissue is formed from floating cells. In the present invention, the rotating culture vessel 2 has the observation window 27 on the front face. Thus, the inner condition can be observed through an imaging camera or various analytical equipments placed toward the observation window 27, and an actual condition can be analyzed through image processing. Based on the condition, the rotation control mechanism 42 can be feedback-controlled, and the timing of liquid culture medium exchange can be automatically determined.

EXAMPLES

Next, rotation cultures were performed using the automatic cell culture apparatus of the present invention and by hand as a control (using RCCS-4D manufactured by Synthecon, the rotation speed was visually controlled). Cartilage tissue formation experiment was carried out using bone marrow cells of Japanese white rabbit to compare the both rotation cultures. The experimental procedure will be described below.

(Experimental Procedure)

(1) Bone marrow cells were collected from the long bones of two Japanese white rabbits, 10 days old, and suspended in 20 ml standard medium.

*Standard Medium: DMEM (Dulbeccco's modified Eagle's medium (DMEM, Sigma, St. Louis Mo.)+10% FBS (fetal bovine serum)+antibiotic-antimycotic (Invitrogen, Carlsbad, Calif.)

(2) Next, the cells were seeded into a 75T flask (BD) together with 15 ml standard medium and cultured in 5% $CO_2$ at 37° C. for 3 weeks.

(3) Next, the cells were removed with trypsin, suspended in a bioreactor medium, and transferred into a 50 cc vessel.

*Bioreactor Medium: DMEM+50 μg/ml ascorbic acid (WAKO)+40 μg/ml L-proline+ITS culture supplement (BD Biosciences), 10-7 dexamethasone (Sigma), 10 ng/ml TGF-β3 (Sigma), and abtiobiotic-antimycotic (BD)

*The 50 cc vessel used in Example is that shown in FIG. 9 to FIG. 15.

*The number of cells used for the culture using the automatic cell culture apparatus (Example) was the same as that for the manual culture (Comparative Example).

(4) The cells were cultured for 2 weeks. The tissue was taken out, macroscopically observed, and sliced into sections. The sections were evaluated by histochemical techniques.

During the liquid culture medium exchange by the automatic cell culture apparatus of the present invention, cellular tissues were not hit by the vessel wall. Furthermore, the liquid culture medium did not leak between each injection needle of the supply syringe and the discharge syringe and the septum seal. It could be observed that the used liquid culture medium in the vessel was exchanged with the new liquid culture medium in sequence from the bottom. There was no accumulated gas in the upper part of the vessel after the liquid culture medium exchange.

(Culture Result)

FIG. 19 shows the appearances of the cartilage tissues formed by the cultures. In FIG. 19, the left image shows the result of the automatic culture (Example) and the right image shows the result of the manual culture (Comparative Example). Macroscopic observations of the cultured cartilage tissues revealed that the tissue by the manual culture was larger than that by the automatic culture.

Figure 20:
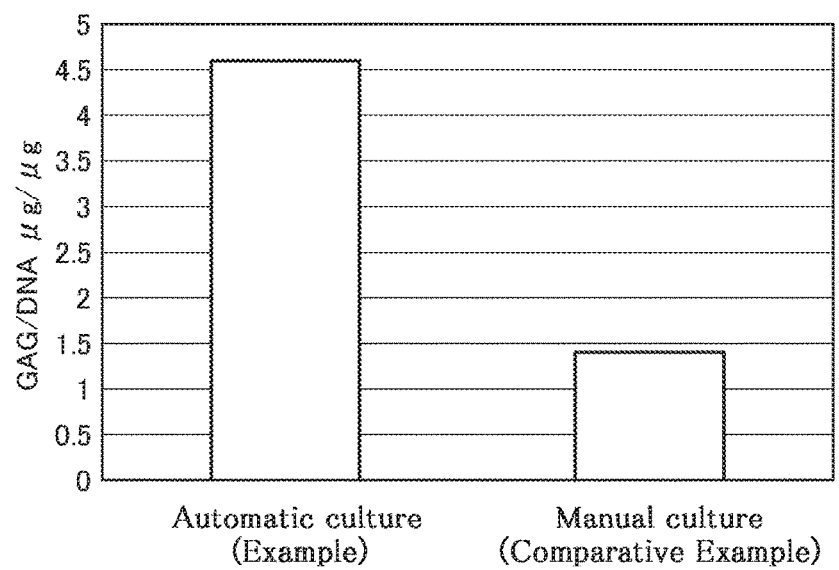
FIG. 20 is a graph showing the result comparing the production amounts of GAG in cartilage matrix.

FIG. 20 is a graph showing the result comparing the production amounts of GAG in the cartilage matrix. In this culture, the production amount by the automatic culture was higher. In the experiments repeated several times, the production amount of GAG in the cartilage matrix by the automatic culture was the same as or higher than that by the manual culture.

Finally, FIG. 21 to FIG. 23 show the results of the histological evaluations on the cartilage tissues formed by the cultures. FIG. 21 are micrographs showing the results of the cartilage tissues stained with Alcian blue. In both tissues, the cartilage matrix was stained light blue, and the rich production of the cartilage matrix was confirmed. Here, the area where the cartilage matrix was stained light blue is indicated by dark color in FIG. 21.

FIG. 22 are micrographs showing the results of the cartilage tissues stained with toluidine blue. In both tissues, the cartilage matrix was stained blue purple, and the rich production of the cartilage matrix was confirmed. In this case, the area where the cartilage matrix was stained blue purple is also indicated by dark color in FIG. 22.

FIG. 23 are micrographs showing the results of the cartilage tissues stained with HE (hematoxylin-eosin). The cartilage tissue was stained blue purple with hematoxylin, and the mature chondrocytes stained blue purple were observed in both tissues by the automatic culture and the manual culture. In this case, the area stained blue purple is also indicated by dark color in FIG. 23. However, cytoplasm, connective tissue in soft tissue, red blood cells, fibrin, endocrine granules, and the like are stained light red or indigo blue with eosin. Thus, each stained area is indicated by similar dark color in a monochrome image, and the cartilage tissue cannot be distinguished in the monochrome image.

As described above, the culture using the automatic cell culture apparatus of the present invention was compared with that by hand while controlling the rotation. The result of the culture of rabbit bone marrow cells with the rotating culture device using the RWV vessel revealed that the automatic culture was equal or superior in quality to the manual culture.

INDUSTRIAL APPLICABILITY

According to the automatic cell culture apparatus of the present invention, even medical institutions not having cell processing center (CPC) in compliance with good manufacturing practice (GMP) can expect clinical application of regenerative medicine, and consequently, the regenerative medicine can be greatly generalized. Typically, it can be used in order to form transplantable cartilage tissues from human bone marrow cells. In addition to the cartilage regeneration, the study of the regenerative medicine has been extended to corneal regeneration for retinal detachment, cataract, and the like, bone regeneration for bone defect and osteoporosis, pancreas (Langerhans island) regeneration for diabetes mellitus and the like, cardiac muscle regeneration for dilated cardiomyopathy and the like, nerve regeneration for Parkinson's disease and Alzheimer's disease, and the like. Hence, the automatic cell culture apparatus of the present invention is supposed to have an advantage in the regenerative medicine in addition to the cartilage regeneration. The automatic cell culture apparatus of the present invention will be generally applicable to the regenerative medicine in addition to the cartilage regenerative medicine in future, and will certainly be the essential and important basic technique for the generalization of the regenerative medicine.

REFERENCE SIGNS LIST

1 Automatic cell culture apparatus
2 Rotating culture vessel
3 Rotating culture device
4 Cool supply box
5 Cool discharge box
6 Shaft direction shifting means
7 XYZ-axis shifting mechanism for supply
8 XYZ-axis shifting mechanism for discharge
9 Closed housing
10 Incubator box
11 Supply syringe
11A Piston
11B Injection needle
12 Discharge syringe
12A Piston
12B Injection needle
13 Rotating shaft
14 Fixing chuck
15 Push up means
16 Fixing chuck
17 Pull up means
18 Culture container
19 Cell suspension supply port
20 Air bleeding port
21 Cell discharge port
22, 22A, 22B, 22C Supply port
23, 23A, 23B, 23C Discharge port
24 Attaching part
25 Intake port
26 Gas permeable membrane
27 Observation window
28 Septum seal
29 Port
30 Cap
31 Inlet flow path
32 Orifice flow path
33 Port
34 Septum seal
35 Cap
36 Concave part
37 Port
38 Rubber plug
39 Inspection door
40 Operation door
41 Air conditioner
42 Rotation control mechanism
43 Door
44 Shaft bearing
45 Linear guide
46 Movable part
47 Door
48 Stacker
49 Stepping motor
50 Rotating shaft
51 Holder
52 Door
53 Stacker
54 Stepping motor
55 Rotating shaft
56 Holder
57 Y-axis shifting mechanism
58 Z-axis shifting mechanism
59 X-axis shifting mechanism
60 U-groove plate
61 Hand
62 Z-axis shifting mechanism
63 Push up plate
64 Y-axis shifting mechanism
65 Z-axis shifting mechanism
66 X-axis shifting mechanism 67 U-groove plate
68 Hand
69 Z-axis shifting mechanism
70 Pull up plate

The invention claimed is:

1. An automatic cell culture apparatus using a rotating culture vessel used for three-dimensional culture of a cell in a nearly gravity-free microgravity environment, the rotating culture vessel including a flat cylindrical culture container having a cylinder axis, being removably attached to an end of a horizontal rotating shaft of a rotating culture device such that the cylinder axis is coaxially arranged to the horizontal rotating shaft as a rotating center, one or more inlets/outlets for supplying a cell and a liquid culture medium at an initial stage and taking out a cultured cell at an appropriate position on the flat cylindrical culture container, and at least one pair of a supply port and a discharge port for exchanging the liquid culture medium on an outer circumferential cylindrical face of the culture container so that the discharge port faces vertically upward when the supply port faces vertically downward, the pair of the supply port and the discharge port being positioned vertically opposite to each other in a state where the discharge port is facing vertically upward when the supply port is facing vertically downward, the discharge port having a first center line vertically extending with passing through a center of the discharge port, the first center line passing through a center axis of the rotating shaft, which serves as the rotating center, and the supply port having a second center line vertically extending with passing through a center of the supply port, the second center line extending without passing through the center axis of the rotating shaft, which serves as the rotating center, the automatic cell culture apparatus comprising:
 a closed housing having an air conditioning function;
 an incubator box of a rotating culture device in a middle chamber of the closed housing;
 a cool supply box storing a supply syringe for supplying a liquid culture medium in a lower chamber of the closed housing; and
 a cool discharge box storing a discharge syringe for collecting a liquid culture medium in an upper chamber of the closed housing;
 each of the incubator box, the cool supply box, and the cool discharge box including a front face having an automatically operated door,
 the rotating culture device having a shaft direction shifting means shifting a horizontal rotating shaft back and forth in a shaft direction, the horizontal rotating shaft being provided in the incubator box,
 the rotating shaft having an end removably installed with the rotating culture vessel,
 a front space of the cool supply box including an XYZ-axis shifting mechanism for supply,
 the XYZ-axis shifting mechanism for supply including a movable part for supply driven by the mechanism, e movable part for supply having a fixing chuck for holding the supply syringe upward and a push up means for pushing a piston up,
 a front space of the cool discharge box including an XYZ-axis shifting mechanism for discharge,
 the XYZ-is shifting mechanism for discharge including a movable part for discharge driven by the mechanism, the movable part for discharge having a fixing chuck for holding the discharge syringe downward and a pull up means for pulling a piston up, and
 each door being opened, the shaft direction shifting means being driven to bring the rotating culture vessel frons the incubator box to a front space, the rotating culture vessel being stopped with the supply port facing downward and the discharge port facing upward, the XYZ-axis shifting mechanism for supply and the fixing chuck being driven to take out the supply syringe from the cool supply box and to locate the supply syringe below the rotating culture vessel, the XYZ-axis shifting mechanism for discharge and the fixing chuck being driven to take out the discharge syringe from the cool discharge box and to locate the discharge syringe above the rotating culture vessel, the XYZ-axis shifting mechanism for supply being driven to airtightly connect the supply syringe to the supply port, simultaneously, the XYZ-axis shifting mechanism for discharge being driven to airtightly connect the discharge syringe to the discharge port, and then the push up means and the pull up means being synchronously driven to exchange a liquid culture medium in the rotating culture vessel.

2. An automatic cell culture apparatus using a rotating culture vessel used for three-dimensional culture of a cell in a nearly gravity-free microgravity environment, the rotating culture vessel including a flat cylindrical culture container having a cylinder axis, being removably attached to an end of a horizontal rotating shaft of a rotating culture device such that the cylinder axis is coaxially arranged to the horizontal rotating shaft as a rotating center, one or more inlets/outlets for supplying a cell and a liquid culture medium at an initial stage and taking out a cultured cell at an appropriate position on the flat cylindrical culture container, and at least one pair of a supply port and a discharge port for exchanging the liquid culture medium on an outer circumferential cylindrical face of the culture container so that the discharge port faces vertically upward when the supply port faces vertically downward, the pair of the supply port and the discharge port being positioned vertically opposite to each other in a state where the discharge port is facing vertically upward when the supply port is facing vertically downward, the discharge port having a first center line vertically extending with passing through a center of the discharge port, the first center line passing through a center axis of the rotating shaft, which serves as the rotating center, and the supply port having a second center line vertically extending with passing through a center of the supply port, the second center line extending without passing through the center axis of the rotating shaft, which serves s the rotating center, wherein a distance between the second center line of the supply port and the rotating center is 0.5r to 0.9r where the culture container has a culture space having a radius of r, the automatic cell culture apparatus comprising:
 a closed housing having an air conditioning function;
 an incubator box of a rotating culture device in a middle chamber of the closed housing;
 a cool supply box storing a supply syringe for supplying a liquid culture medium in a lower chamber of the closed housing; and
 a cool discharge box storing a discharge syringe for collecting a liquid culture medium in an upper chamber of the closed housing;
 each of the incubator box, the cool supply box, and the cool discharge box including a front face having an automatically operated door,
 the rotating culture device having a shaft direction shifting means shifting a horizontal rotating shaft back and forth in a shaft direction, the horizontal rotating shaft being provided in the incubator box, the rotating shaft having an end removably installed with the rotating culture vessel, a front space of the cool supply box including an XYZ-axis shifting mechanism for supply, the XYZ-axis shifting mechanism for supply including a movable part for supply driven by the mechanism, the movable part for supply having a fixing chuck for holding the supply syringe upward and a push up means for pushing a piston up, a front space of the cool discharge box including an XYZ-axis shifting mechanism for discharge, the XYZ-axis shifting mechanism for discharge including a movable part for discharge driven by the mechanism, the movable part for discharge having a fixing chuck for holding the discharge syringe downward and a pull up means for pulling a piston up, and each door being opened, the shaft direction shifting means being driven to bring the rotating culture vessel from the incubator box to a front space, the rotating culture vessel being stopped with the supply port facing downward and the discharge port facing upward, the XYZ-axis shifting mechanism for supply and the fixing chuck being driven to take out the supply syringe from the cool supply box and to locate the supply syringe below the rotating culture vessel, the XYZ-axis shifting mechanism for discharge and the fixing chuck being driven to take out the discharge syringe from the cool discharge box and to locate the discharge syringe above the rotating culture vessel, the XYZ-axis shifting mechanism for supply being driven to airtightly connect the supply syringe to the supply port, simultaneously, the XYZ-axis shifting mechanism for discharge being driven to airtightly connect the discharge syringe to the discharge port, and then the push up means and the pull up means being synchronously driven to exchange a liquid culture medium in the rotating culture vessel.

* * * * *